US010414858B2

(12) United States Patent
Dauenhauer et al.

(10) Patent No.: US 10,414,858 B2
(45) Date of Patent: Sep. 17, 2019

(54) METHODS OF FORMING DIOL COMPOUNDS

(71) Applicant: REGENTS OF THE UNIVERSITY OF MINNESOTA, Minneapolis, MN (US)

(72) Inventors: Paul J. Dauenhauer, Minneapolis, MN (US); Charles Spanjers, Minneapolis, MN (US); Kechun Zhang, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 30 days.

(21) Appl. No.: 15/491,236

(22) Filed: Apr. 19, 2017

(65) Prior Publication Data
US 2017/0297983 A1 Oct. 19, 2017

Related U.S. Application Data

(60) Provisional application No. 62/324,630, filed on Apr. 19, 2016.

(51) Int. Cl.
C07C 29/151 (2006.01)
C08G 63/85 (2006.01)
C07C 29/149 (2006.01)

(52) U.S. Cl.
CPC .......... *C08G 63/85* (2013.01); *C07C 29/149* (2013.01)

(58) Field of Classification Search
CPC .................................................. C07C 29/151
See application file for complete search history.

(56) References Cited

U.S. PATENT DOCUMENTS

| 3,859,369 | A | 1/1975 | Copelin |
| 4,782,167 | A | 11/1988 | Rao |
| 5,536,854 | A | 7/1996 | Weyer |
| 6,204,417 | B1 | 3/2001 | Fischer |

FOREIGN PATENT DOCUMENTS

| CN | 104923218 A | 9/2015 |
| CN | 105131261 A | 12/2015 |
| EP | 0276012 A2 | 1/1988 |
| EP | 0589314 A1 | 9/1993 |

OTHER PUBLICATIONS

Tapin (ACS Catalysis 3 (2013) 2327-2335).*
Besson, "Conversion of biomass into chemicals over metal catalysts" 2014 *Chem. Rev.*, 114:1827-1870.
Deshpande, "Tailoring of activity and selectivity using bimetallic catalyst in hydrogenation of succinic acid" 2002 *Catal. Commun.*, 3(7):269-274.
Doak, "Effect of substituents upon melting points of linear polyesters" 1955 *J. Polym. Sci.*, 18(88):215-226.
Geilen, "Selective and flexible transformation of biomass-derived platform chemicals by a multifunctional catalytic system" Jul. 2010 *Angew. Chemie*, 122:5642-5646.
Geilen, "Selective homogeneous hydrogenation of biogenic carboxylic acids with [Ru(TriPhos)H]+: a mechanistic study" Sep. 2011 *J. Am. Chem. Soc.*, 133(36):14349-14358.
Green, "Diels-Alder cycloaddition of 2-methylfuran and ethylene for renewable toluene" 2016 *Appl. Catal. B Environ.*, 180:487-496.
Hong, "Hydrogenation of succinic acid to tetrahydrofuran (THF) over ruthenium—carbon composite (Ru—C) catalyst" Jan. 2014 *Appl. Catal. A Gen.*, 469:466-471.
Huang, "Preparing acid-resistant Ru-based catalysts by carbothermal reduction for hydrogenation of itaconic acid" 2015 *RSC Adv.*, 5:97256-97263.
Isikgor, "Lignocellulosic biomass: a sustainable platform for the production of bio-based chemicals and polymers" 2015 *Polymer Chem.*, 25(6): 4497-4559.
Kuraray, "Industrial alcohols, diols" Online: http://www.kuraray.com/products/chemical/diols.html.
Li, "Aqueous-phase hydrogenation of biomass-derived itaconic acid to methyl-γ-butyrolactone over Pd/C catalysts: Effect of pretreatments of active carbon" 2015 *Catal. Commun.*, 61:92-96.
Li, "Ruthenium complexes of tetradentate bipyridine ligands: highly efficient catalysts for the hydrogenation of carboxylic esters and lactones " 2014 *Green Chem.*, 16:4081-4085.
Liu, "A sustainable process for the production of 2-methyl-1,4-butanediol by hydrogenation of biomass-derived itaconic acid" 2016 *Catal. Today*, 274:88-93.
Loman, "Effect of methyl groups on the thermal properties of polyesters from methyl substituted 1,4-butanediols and 4,4'-biphenyldicarboxylic acid" 1995 *J. Polym. Sci. Part A Polym. Chem.*, 33:493-504.
Longley, "β-Methyl-δ-Valerolactone [Valeric acid, 5-hydroxy-3-methyl-, δ-lactone]" 1963 *Organic Synthesis Coll.*, 4:677.

(Continued)

*Primary Examiner* — Kuo Liang Peng
(74) *Attorney, Agent, or Firm* — Mueting, Raasch & Gebhardt, PA

(57) ABSTRACT

Methods of forming a $C_4$ to $C_7$ diol compound, the methods including a first step of reacting a $C_4$ to $C_7$ dicarboxylic acid with hydrogen ($H_2$) gas on a first heterogeneous catalyst at a first temperature and a first pressure to form a $C_4$ to $C_7$ lactone; and a subsequent step of reacting the lactone with hydrogen ($H_2$) gas on a second heterogeneous catalyst at a second temperature and a second pressure, wherein the second temperature is lower than the first temperature. Also disclosed are methods of forming a solvent, the methods including reacting a $C_4$ to $C_7$ dicarboxylic acid with hydrogen ($H_2$) gas on a first heterogeneous catalyst at a first temperature and a first pressure to form a solvent. Further disclosed herein are methods that include reacting mevalonolactone with hydrogen ($H_2$) gas on a second heterogeneous catalyst at a second temperature and a second pressure to form a diol compound.

17 Claims, 20 Drawing Sheets

(56) References Cited

OTHER PUBLICATIONS

Luque, "Water-tolerant Ru-Starbon® materials for the hydrogenation of organic acids in aqueous ethanol" May 2010 *Catal. Commun.*, 11:928-931.

Ly, "Insights into the Oxidation State and Location of Rhenium in Re-Pd/TiO2 Catalysts for Aqueous-Phase Selective Hydrogenation of Succinic Acid to 1,4-Butanediol as a Function of Palladium and Rhenium Deposition Methods" Jun 2015 *ChemCatChem.*, 7:2161-2178.

Ly, "Effect of addition mode of Re in bimetallic Pd—Re/TiO2 catalysts upon the selective aqueous-phase hydrogenation of succinic acid to 1,4-butanediol" 2012 *Top. Catal.*, 55:466-473.

Marenich, "Universal solvation model based on solute electron density and on a continuum model of the solvent defined by the bulk dielectric constant and atomic surface tensions" May 2009 *J. Phys. Chem. B*, 113(18):6378-6396.

Minh, "Aqueous-phase hydrogenation of biomass-based succinic acid to 1, 4-butanediol over supported bimetallic catalysts" 2010 *Top. Catal.*, 53(15-18):1270-1273.

Ochterski, "Thermochemistry in Gaussian" in *Gaussian Inc, Pittsburgh, PA*; 2000, pp. 1-17.

Okabe, "Biotechnological production of itaconic acid and its biosynthesis in Aspergillus terreus" Sep. 2009 *Appl. Microbiol. Biotechnol.*, 84(4):597-606.

Palaskar, "Synthesis of Biobased Polyurethane from Oleic and Ricinoleic Acids as the Renewable Resources via the AB-Type Self-Condensation Approach" 2010 *Biomacromolecules*, 11:1202-1211.

Phua, "Mechanical properties and structure development in poly(butylene succinate)/organo-montmorillonite nanocomposites under uniaxial cold rolling eXPRESS" 2011 *Polymer Letters*, 5:93-103.

Primo, "Synergy between the metal nanoparticles and the support for the hydrogenation of functionalized carboxylic acids to diols on Ru/TiO2" 2011 *Chem. Commun. (Camb).*, 47(12):3613-3615.

Schneiderman, "Chemically Recyclable Biobased Polyurethanes" 2016 *ACS Macro Lett.*, 5(4):515-518.

Shabaker, "Sn-modified Ni catalysts for aqueous-phase reforming: Characterization and deactivation studies" 2005 *J. Catal.*, 231:67-76.

Shao, "Aqueous-Phase Hydrogenation of Succinic Acid to γ-Butyrolactone and Tetrahydrofuran over Pd/C, Re/C, and Pd—Re/C Catalysts" 2014 *Ind. Eng. Chem. Res.*, 53(23): 9638-9645.

Spanjers, "Hybrid Catalytic Process to Biomass-Derived Diol Monomers" Center for Sustainable Polymers meeting, Apr. 21, 2016, Minneapolis MN.

Spanjers, "Branched Diol Monomers from the Sequential Hydrogenation of Renewable Carboxylic Acids" 2016 *Chem Cat Chem.*, 6(8):3031-3035.

Steiger, "Biochemistryofmicrobialitaconicacidproduction" Feb. 2013 *Front. Microbiol.*, 4:1-5.

Straathof, "Transformation of biomass into commodity chemicals using enzymes or cells" 2014 *Chem. Rev.*, 114:1871-1908.

Tapin, "Study of Monometallic Pd/TiO2 Catalysts for the Hydrogenation of Succinic Acid in Aqueous Phase" 2013 *ACS Catal.*, 3(10:2327-2335.

Wang, "Production of mesaconate in *Escherichia coli* by engineered glutamate mutase pathway" Jul 2015 Metab. Eng., 30:190-196.

Werpy, *Top Value Added Chemicals from Biomass. Volume 1-Results of Screening for Potential Candidates from Sugars and Synthesis Gas*, DTIC Document, 2004.

Wojcik, "Hydrogenolysis of Alcohols to Hydrocarbons" 1933 *J. Am. Chem. Soc.*, 55(3):1293-1294.

Xiong, "Scalable production of mechanically tunable block polymers from sugar" Jun. 2014 *Proc. Natl. Acad. Sci.*, 111(23):8357-8362.

\* cited by examiner

METHODS OF FORMING DIOL COMPOUNDS

PRIORITY

This application claims priority to U.S. Provisional Application No. 62/324,630, entitled, METHODS OF FORMING DIOL COMPOUNDS", the entire disclosure of which is incorporated herein by reference thereto.

GOVERNMENT FUNDING

This invention was made with government support under CHE-1413862 awarded by the National Science Foundation. The government has certain rights in the invention.

BACKGROUND

The current petrochemical industry is based on the inexpensive and efficient transformation of a few platform chemicals into a wide array of products including solvents, fine chemicals, and monomers for modern plastics. Recently, concerns over sustainability have motivated a return to natural feedstocks; this trend is particularly evident in the polymer industry where consumer awareness of the adverse environmental impacts of nondegradable plastics has driven the commercialization of biodegradable polymers (e.g., the polyesters polylactide and polyhydroxyalkanoates). Despite efforts over the past decade, there exist few methods for efficient, environmentally benign processes for monomer synthesis from biomass.

Organic acids obtained via fermentation of glucose provide an opportunity for synthesis of diols and triols from biomass. Itaconic acid (IA) was termed one of the top-12 building block chemicals in 2004 due to its potential value as a precursor for C5 chemicals (e.g., 2-methyl-1,4-butanediol and (α or β)-methyl-γ-butyrolactone) (T. Werpy, G. Petersen, A. Aden, J. Bozell, J. Holladay, J. White, A. Manheim, D. Eliot, L. Lasure, S. Jones, *Top Value Added Chemicals from Biomass. Volume* 1-*Results of Screening for Potential Candidates from Sugars and Synthesis Gas*, DTIC Document, 2004.). Globally, 80,000 tons of IA are produced per year using *Aspergillus terreus* in a high yielding fermentation process (0.72 g/g from glucose, with titers of up to 86 g/L) (M. G. Steiger, M. L. Blumhoff, D. Mattanovich, M. Sauer, *Front. Microbiol.* 2013, 4, 1-5; and M. Okabe, D. Lies, S. Kanamasa, E. Y. Park, *Appl. Microbiol. Biotechnol.* 2009, 597-606). Mesaconic acid (MA), an isomer of IA, has similar potential as a precursor and was recently produced using *E. coli* (J. Wang, K. Zhang, Metab. Eng. 2015, 30, 190-196). The low cost of itaconic acid (~$2 kg$^{-1}$), enables its use in synthetic resins, plastics, rubbers, surfactants and oil additives (M. Besson, P. Gallezot, C. Pinel, *Chem. Rev.* 2014, 114, 1827-1870; and A. J. J. Straathof, *Chem. Rev.* 2014, 114, 1871-1908). However, the current production capacity of itaconic acid exceeds its demand.

Mevalonic acid (MLA) is a third organic acid efficiently produced from the fermentation of carbohydrates (~80 g L$^{-1}$ titer using *E. coli*) (M. Xiong, D. K. Schneiderman, F. S. Bates, M. A. Hillmyer, K. Zhang, *Proc. Natl. Acad. Sci.* 2014, 111, 8357-8362). MLA is a potentially valuable precursor for synthesis of C6 alcohols, ethers and lactones. However, there are few reports outlining efficient, aqueous-based, processes for production of diols from these C5 and C6 acids.

A prominent challenge in replacing petrochemical polymers with bio-derived alternatives is the efficient transformation of biomass into useful monomers. More efficient methods of converting carboxylic acid containing compounds, for example from biomass, to more valuable and useful compounds, for example monomers, are therefore necessary.

SUMMARY

Disclosed herein are methods of forming a $C_4$ to $C_7$ diol compound, the methods including a first step of reacting a $C_4$ to $C_7$ dicarboxylic acid with hydrogen ($H_2$) gas on a first heterogeneous catalyst at a first temperature and a first pressure to form a $C_4$ to $C_7$ lactone; and a subsequent step of reacting the lactone with hydrogen ($H_2$) gas on a second heterogeneous catalyst at a second temperature and a second pressure, wherein the second temperature is lower than the first temperature.

Disclosed herein are methods of forming a $C_4$ to $C_7$ diol compound, the methods including a first step of reacting a $C_4$ to $C_7$ dicarboxylic acid according to formula II

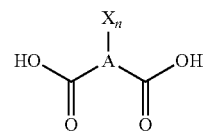

(II)

where X is independently selected from H, —OH, alkyl, alkenyl; n is 1 or 2; and A is a $C_2$ to $C_4$ substituted or unsubstituted alkyl radical or a $C_2$ to $C_4$ substituted or unsubstituted alkenyl radical with hydrogen ($H_2$) gas on a first heterogeneous catalyst at a first temperature and a first pressure to form a $C_4$ to $C_7$ lactone of formula III

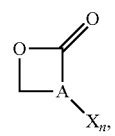

(III)

wherein X, A and n are as defined above; a subsequent step of reacting the lactone of formula III with hydrogen ($H_2$) gas on a second heterogeneous catalyst at a second temperature and a second pressure to form a diol of formula I

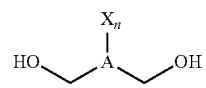

(I)

where X, A and n are as defined above, and wherein the second temperature is lower than the first temperature; and a further step of converting the diol of formula I into branched polymers.

Disclosed herein are methods of forming a solvent, the method including reacting a $C_4$ to $C_7$ dicarboxylic acid with hydrogen ($H_2$) gas on a first heterogeneous catalyst at a first temperature and a first pressure to form a solvent.

The above summary of the invention is not intended to describe each disclosed embodiment or every implementation of the invention. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1B:
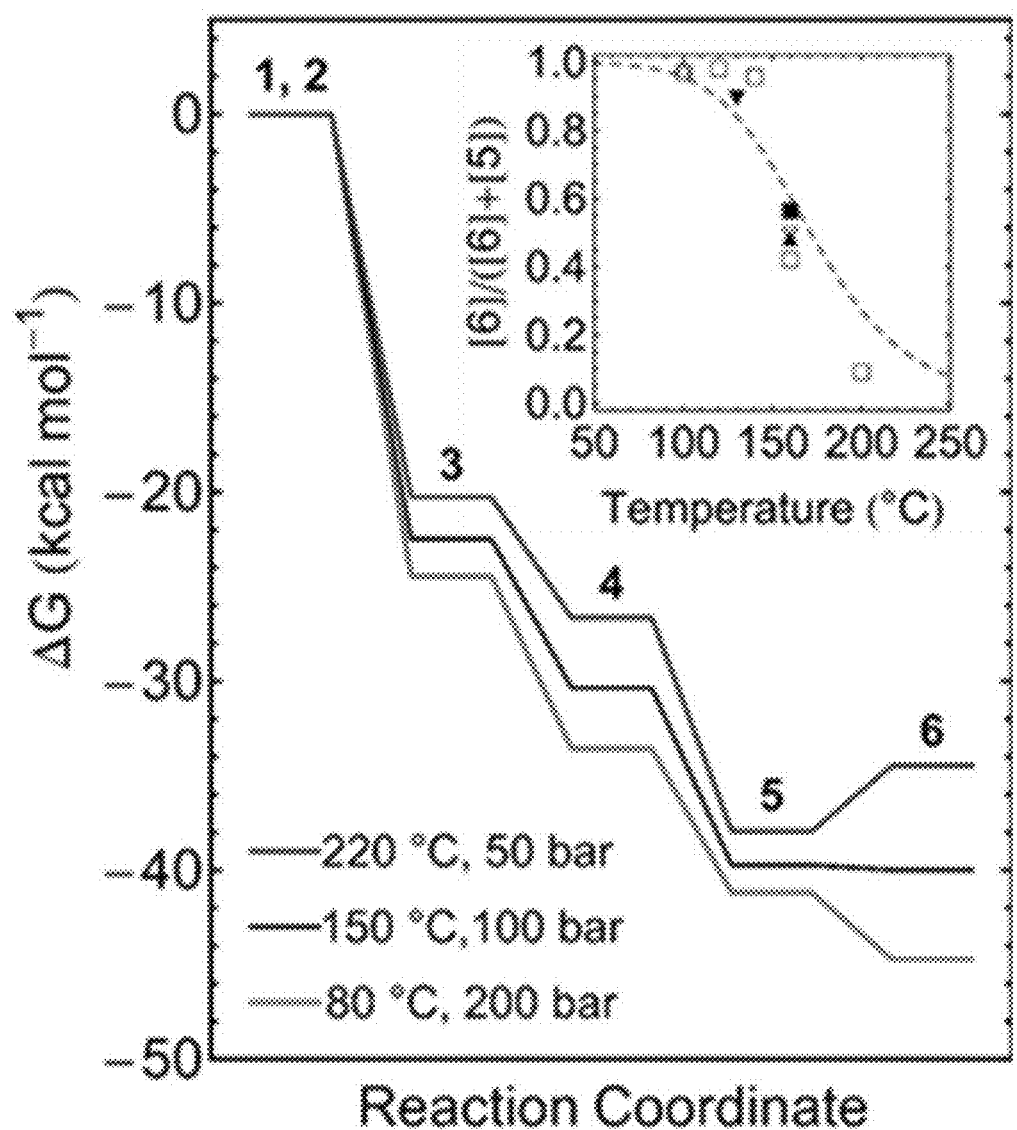
FIG. 1B shows a calculated reaction energy diagram for the hydrogenation of itaconic acid (1) and mesaconic acid (2) to 2-methyl-1,4-butanediol (6) for three different sets of temperatures and pressures demonstrating high pressure and low temperature promote 6 formation. The inset of FIG. 1B shows theoretical temperature dependence (dashed line) and experimental overlay (markers) for the equilibrium [6]/([6]+[5]) ratio at $H_2$ pressure of 140 bar.

Disclosed herein are methods for the synthesis of multifunctional alcohols from acids using heterogeneous catalysts in aqueous media. Consideration and understanding of these methods may be guided by thermodynamic calculations, with specific regard to two sequential reaction steps: (1) reduction of the acid to a lactone at high temperature and high $H_2$ pressure followed by (2) subsequent reduction of the lactone to the corresponding diol or triol at high $H_2$ pressure and low temperature. For example, conversion of itaconic acid to (α or β)-methyl-γ-butyrolactone was achieved with 95% selectivity at a turnover frequency of 1.2 $min^-$ over Pd/C at 240° C. Subsequent conversion of (α or β)-methyl-γ-butyrolactone to 2-methyl-1,4-butanediol was achieved with a yield of 80% with Ru/C at 100° C. Disclosed methods are therefore an efficient method for the production of lactones, diols, and triols, which are all valuable monomers for synthesis of bio-derived branched polyesters.

Disclosed herein are methods of forming multifunctional alcohols or more specifically diol compounds. As used herein, "diol compound" refers to a compound that includes at least two hydroxyl groups. Triol compounds (compounds having three hydroxyl groups) and polyols (compounds having multiple hydroxyl groups) are diol compounds, as defined herein. In some embodiments, the at least two hydroxyl groups can be opposing terminal hydroxyl groups, meaning that one hydroxyl group is attached to a carbon at one end of the carbon chain and a second hydroxyl group is attached to the carbon at the opposite end of the carbon chain. In some embodiments, diol compounds that can be formed can include $C_4$ to $C_{10}$ diol compounds, in some embodiments, $C_4$ to $C_9$ diol compounds, in some embodiments $C_4$ to $C_7$ diol compounds and in some embodiments $C_4$ to $C_6$ diol compounds. Compounds described by their carbon number (e.g., $C_4$ to $C_7$) can include straight chain, branched chain or cyclic structures that include the noted amount of carbon atoms. Illustrative, non-limiting examples of diol compounds include, for example 1,4-butanediol, 1,5-pentanediol, 1,6-hexanediol, 2-methyl-1,4-butanediol, 3-methyl-1,5-pentanediol, 3-methyl-1,3,5-pentanetriol and 1,2,4-butanetriol.

Specific illustrative diol compounds include those of formula I:

where X is independently selected from H, —OH, alkyl and alkenyl; n can be 1 or 2; A is a $C_2$ to $C_4$ substituted or unsubstituted alkyl radical or a $C_2$ to $C_4$ substituted or unsubstituted alkenyl radical. In some embodiments, X is —OH. In some embodiments, X is an alkyl selected from methyl (—$CH_3$), ethyl (—$CH_2CH_3$), propyl (—CH$_2$CH$_2$CH$_3$), isopropyl (—CH$_2$(CH$_3$)(CH$_3$)), butyl (—CH$_2$CH$_2$CH$_2$CH$_3$), sec-butyl (—CH(CH$_3$)(CH$_2$CH$_3$)), isobutyl (—CH$_2$CH(CH$_3$)(CH$_3$)), or tert-butyl (—C(CH$_3$)$_3$).

Disclosed methods begin with dicarboxylic acids. As used herein a "dicarboxylic acid compound" or "dicarboxylic acid" refers to a compound that includes at least two carboxylic acid groups. In some embodiments, the at least two carboxylic acid groups are opposing terminal carboxylic acid groups, meaning that one carboxylic acid group is attached to a carbon at one end of the carbon chain and a second carboxylic acid group is attached to the carbon at the opposite end of the carbon chain. In some embodiments, dicarboxylic acid compounds that can be utilized can include C$_4$ to C$_{10}$ dicarboxylic acid compounds, in some embodiments, C$_4$ to C$_9$ dicarboxylic acid compounds, in some embodiments C$_4$ to C$_7$ dicarboxylic acid compounds and in some embodiments C$_4$ to C$_6$ dicarboxylic acid compounds. Compounds described by their carbon number (e.g., C$_4$ to C$_7$) can include straight chain, branched chain or cyclic structures that include the noted amount of carbon atoms. The carbon number of a dicarboxylic acid compounds includes all of the carbon atoms in the compound, specifically including the carbons which form the carboxylic acids, e.g. itaconic acid (OH(O=)CCH$_2$C(=CH$_2$)C(=O)OH) is a C$_5$ dicarboxylic acid. The dicarboxylic acid compounds could also include other functional groups, including but not limited to additional carboxylic acid groups. Illustrative, non-limiting examples of dicarboxylic acid compounds include, for example itaconic acid (IA) (a C$_5$ dicarboxylic acid compound), mesaconic acid (MA) (a C$_5$ dicarboxylic acid compound), glutaric acid (a C$_5$ dicarboxylic acid compound), glutaconic acid (a C$_5$ dicarboxylic acid compound), adipic acid (a C$_6$ dicarboxylic acid compound), muconic acid (a C$_6$ dicarboxylic acid compound), succinic acid (a C$_4$ dicarboxylic acid compound), fumaric acid (a C$_4$ dicarboxylic acid compound), maleic acid (a C$_4$ dicarboxylic acid compound), mevalonic acid (a C$_6$ dicarboxylic acid compound), citaconic acid (a C$_5$ dicarboxylic acid compound), methylsuccinic acid (a C$_5$ dicarboxylic acid compound), and malic acid (a C$_4$ dicarboxylic acid compound).

Specific illustrative carboxylic acid compounds are those of formula II:

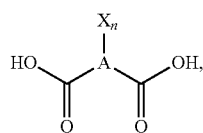

(II)

where X is independently selected from H, —OH, alkyl and alkenyl; n is 1 or 2; A is a C$_2$ to C$_4$ substituted or unsubstituted alkyl radical or a C$_2$ to C$_4$ substituted or unsubstituted alkenyl radical. In some embodiments, X is —OH. In some embodiments, X is an alkyl selected from methyl (—CH$_3$), ethyl (—CH$_2$CH$_3$), propyl (—CH$_2$CH$_2$CH$_3$), isopropyl (—CH$_2$(CH$_3$)(CH$_3$)), butyl (—CH$_2$CH$_2$CH$_2$CH$_3$), sec-butyl (—CH(CH$_3$)(CH$_2$CH$_3$)), isobutyl (—CH$_2$CH(CH$_3$)(CH$_3$)), or tert-butyl (—C(CH$_3$)$_3$).

Disclosed methods convert dicarboxylic acids into lactones and in some embodiments the lactones are converted into diols. As used herein "lactone compound" refers to a compound that includes at least a lactone. In some embodiments, lactone compounds that can be produced can include C$_4$ to C$_{10}$ lactone compounds, in some embodiments, C$_4$ to C$_9$ lactone compounds, in some embodiments C$_4$ to C$_7$ lactone compounds and in some embodiments C$_4$ to C$_6$ lactone compounds. Lactone compounds described by their carbon number (e.g., C$_4$ to C$_7$) can include cyclic structures that include the noted amount of carbon atoms only within the ring or cyclic structures that include one or more than one of the noted amount of carbon atoms as substituents on the cyclic structure. The lactone compounds could also include substituents on the ring and could also include other functional groups as substituents on the ring. Illustrative, non-limiting examples of lactone compounds can include four membered lactone rings (β-lactone), five membered lactone rings (γ-lactone), six membered lactone rings (δ-lactone), and seven membered lactone rings (ε-lactone). Illustrative, non-limiting examples of lactone compounds include, for example, δ-valerolactone, ε-caprolactone, γ-butyrolactone, mevalonolactone, anhydromevalonolactone, α-methyl-γ-butyrolactone, β-methyl-γ-butyrolactone, α-hydroxy-γ-butyrolactone, and β-hydroxy-γ-butyrolactone.

Specific illustrative lactone compounds are those of formula III:

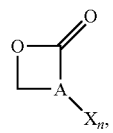

(III)

where X is independently selected from H, —OH, alkyl and alkenyl; n is 1 or 2; A is a C$_2$ to C$_4$ substituted or unsubstituted alkyl radical or a C$_2$ to C$_4$ substituted or unsubstituted alkenyl radical. In some embodiments, X is —OH. In some embodiments, X is an alkyl selected from methyl (—CH$_3$), ethyl (—CH$_2$CH$_3$), propyl (—CH$_2$CH$_2$CH$_3$), isopropyl (—CH$_2$(CH$_3$)(CH$_3$)), butyl (—CH$_2$CH$_2$CH$_2$CH$_3$), sec-butyl (—CH(CH$_3$)(CH$_2$CH$_3$)), isobutyl (—CH$_2$CH(CH$_3$)(CH$_3$)), or tert-butyl (—C(CH$_3$)$_3$).

Disclosed methods can include two steps. The two steps can be aqueous phase reactions, be carried out in aqueous conditions, or be carried out in an aqueous phase reactor. In some embodiments, the two steps are sequential. The first step converts a dicarboxylic acid compound to a lactone compound and the second step converts the lactone compound to a diol compound. The sequential nature of the two steps allows the conditions (e.g., pressure, temperature, etc.) to be individually controlled for each step. This individual control of the two steps can offer the overall advantage of higher selectivity and higher conversion. With regard to the first step, thermodynamic calculations show that hydrogenation of a dicarboxylic acid to a lactone is thermodynamically downhill in free energy, suggesting that the lactone is the thermodynamically-preferred product for all high temperature, high H$_2$ pressure conditions of hydrogenating a dicarboxylic acid, when the reaction is quenched at the formation of the lactone. With regard to the second step, conversion of a lactone to the diol is unfavorable at high temperature and low H$_2$ pressure conditions but is favored at lower temperatures and higher H$_2$ pressures.

Reaction conditions, e.g., temperature, pressure, or both, of each step can be controlled as would be known to those of skill in the art. For example, catalytic reactors or systems including catalytic reactors can control the pressure (e.g., addition or subtraction of gases—reactive, non-reactive, or combinations thereof), temperature, impeller speed (e.g. rate of gas-to-liquid mass transfer), liquid volume level, or combinations thereof.

A first step in disclosed methods includes a step of reacting a dicarboxylic acid with hydrogen ($H_2$) gas on or in the presence of a first heterogeneous catalyst at a first temperature and a first pressure to form a lactone. Illustrative first catalysts can include for example palladium (Pd), platinum (Pt), rhodium (Rh), nickel (Ni), copper chromite ($Cu_2Cr_2O_5$), ruthenium (Ru), or combinations thereof. In some embodiments, the first heterogeneous catalyst can include palladium (Pd). The first heterogeneous catalyst can be supported or non-supported. Supported catalysts are catalysts that are dispersed on a second material that may enhance the effectiveness of the catalyst, minimize the cost, or both. In some embodiments first heterogeneous catalysts can be supported on carbon (C) for example activated carbon, alumina ($Al_2O_3$), silica ($SiO_2$), titania ($TiO_2$), or combinations thereof.

Disclosed first steps can be carried out or undertaken at a first temperature. In some embodiments, the first temperature can be characterized as a relatively high temperature. Use of relatively high temperatures in the first step may increase the rate of reaction of the dicarboxylic acid into the lactone. However, increasing the temperature of the first step also decreases the selectivity of the first step. Therefore, typically utilized temperatures may be a compromise between a desired rate and a desired level of selectivity. In some embodiments, the first temperature can be at least 160° C., at least 200° C. or at least 240° C., for example.

Disclosed first steps can be carried out or undertaken at a first pressure. The first pressure is a measure of the volume or pressure of reactive gas, e.g., $H_2$ in the reactor in addition to the saturation pressure of solvent in the gas-phase. In some embodiments, the first pressure can be at least 35 bar, at least 55 bar or at least 70 bar. In some embodiments, the first pressure can range from 70 bar to 140 bar. Higher $H_2$ pressures result in an increased rate of gas-to-liquid mass transfer, an increased concentration of $H_2$ in the liquid phase, and an increased concentration of hydrogen on the catalyst surface, all of which may have a positive effect on the rate of reaction. In some embodiments a first step can be carried out at a first temperature of 240° C. and a pressure of 140 bar $H_2$, for example.

A second step in disclosed methods includes a step of reacting the lactone with hydrogen ($H_2$) gas on or in the presence of a second heterogeneous catalyst at a second temperature and a second pressure to form a diol. Illustrative second catalysts can include ruthenium (Ru), palladium (Pd), platinum (Pt), rhenium (Re), or combinations thereof. In some embodiments, the second heterogeneous catalyst can include ruthenium (Ru). The second heterogeneous catalyst can be supported or non-supported. In some embodiments second heterogeneous catalysts can be supported on carbon (C) for example activated carbon, alumina ($Al_2O_3$), silica ($SiO_2$), titania ($TiO_2$), or combinations thereof.

Disclosed second steps can be carried out or undertaken at a second temperature. In disclosed methods, the second temperature can be lower than the first temperature. Use of relatively low temperatures in the second step can maintain a desired level of selectivity of the reaction. However, at temperatures that are too low, the rate of reaction will become increasingly undesirable. Therefore, temperatures for use in the second step may be a compromise between a desired level of selectivity and an efficient or desired rate of reaction. In some embodiments, the second temperature can be less than 150° C., less than 140° C., or less than 110° C., for example. In some embodiments, the second temperature can be at least 60° C.

Disclosed second steps can be carried out or undertaken at a second pressure. The second pressure is a measure of the volume or pressure of reactive gas, e.g., $H_2$ in the reactor, or can refer to the combined pressure of the reactive gas, a non-reactive gas such as $N_2$ or Ar, and the vapor pressure of the solvent. In some embodiments, a second non-reactive gas can also be added to the reaction chamber in order to increase the pressure in the reactor. In some embodiments, the second pressure can be at least 100 bar, at least 120 bar or at least 140 bar. In some embodiments a second step can be carried out at a second temperature of 100° C. and a second pressure of 140 bar.

Disclosed methods can also include additional, optional steps. For example, once a diol compound has been formed methods can include reacting the diol compound with one or more additional reactants. In some specific illustrative embodiments, the diol compounds can be converted into polymers, e.g., the diols can be utilized as monomers. In some more specific illustrative embodiments, the diol compounds can be converted into branched polymers. In some embodiments, diols prepared using disclosed methods can be utilized to form polyesters, for example, using condensation polymerization (for example) with a catalyst. Specifically, a diol can be combined with a dicarboxylic acid in the presence of a catalyst to prepare polyester polymers. Properties of the polymers can be modified by altering possible substituents on the diol, the dicarboxylic acid, or both. Polymers having various properties can therefore be obtained. In some embodiments such polymers may be useful for applications such as coatings, adhesives, sealants, elastomers, foams, or combinations thereof.

Optionally, dicarboxylic acid compounds utilized in disclosed methods can be obtained from biomass. In some specific embodiments, dicarboxylic acid compounds contained in a composition derived from biomass can be utilized in disclosed methods. In some embodiments, a composition obtained from biomass can be subjected to one or more separation or reaction steps before the composition is utilized in disclosed methods as a composition that contains dicarboxylic acids. For example, a fermentation broth could be utilized directly as a composition that contains dicarboxylic acid compounds and subjected to a disclosed method(s). Alternatively, a fermentation broth could be separated, e.g., via filtration, to remove components such as cells, etc. before it is utilized as a composition that contains dicarboxylic acid compounds and subjected to a disclosed method(s).

Also disclosed herein are methods of forming diol compounds, e.g., $C_4$ to $C_{10}$ diol compounds by reacting a $C_4$ to $C_{10}$ dicarboxylic acid compound with hydrogen ($H_2$) gas on a heterogeneous ruthenium (Ru) containing catalyst. In some embodiments, the step of reacting the dicarboxylic acid compound could be undertaken in aqueous conditions.

Also disclosed herein are methods of forming a solvent or a solvent mixture by reacting a $C_4$ to $C_{10}$ dicarboxylic acid compound with hydrogen ($H_2$) gas on a heterogeneous catalyst at a first temperature and a first pressure to form a solvent or solvent composition.

Scheme 1 depicts illustrative examples of conversions that can be affected by disclosed methods. Specifically, Scheme 1 depicts an efficient catalytic method for the aqueous reduction of organic acids such as IA to methyl-γ-butyrolactone (MGBL) and then to 2-methyl-1,4-butanediol (MBDO). Scheme 1 also depicts the method being used to reduce both MA and MLA. Such a method could enable the efficient synthesis of branched $C_5$ and $C_6$ diols, which may be useful for the synthesis of polyesters as well as numerous other applications.

Scheme 1

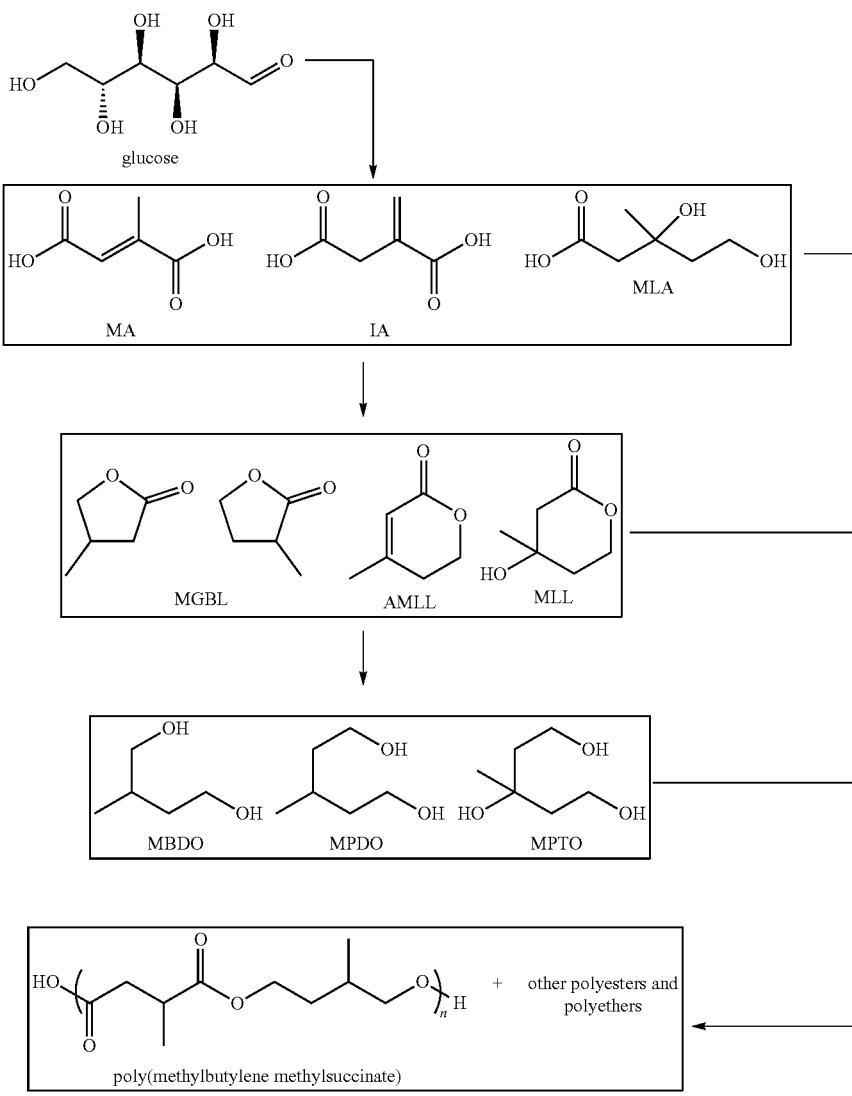

Hydrogenation of multifunctional carboxylic acids has been evaluated for the related four-carbon molecule, succinic acid (SA), which proceeds through 4-hydroxybutyric acid and γ-butyrolactone as intermediates to BDO. SA is used in combination with a diol to prepare polyesters or as an intermediate for the synthesis of either 1,4-butanediol (BDO) or tetrahydrofuran (THF). The former may be used as a chain extender in polyurethane synthesis, for example, while the latter is useful both as a solvent and as a monomer for polyether synthesis. Specific to the reduction of SA, heterogeneous catalysts including Re/C (Z. Shao, C. Li, X. Di, Z. Xiao, C. Liang, *Ind. Eng. Chem. Res.* 2014, 53, 9638-9645), Pd—Re/C (D. P. Minh, M. Besson, C. Pinel, P. Fuertes, C. Petitjean, *Top. Catal.* 2010, 53, 1270-1273), Pd—Re/TiO$_2$ (B. K. Ly, D. P. Minh, C. Pinel, M. Besson, B. Tapin, F. Epron, C. Especel, *Top. Catal.* 2012, 55, 466-473; and B. K. Ly, B. Tapin, M. Aouine, P. Delichere, F. Epron, C. Pinel, C. Especel, M. Besson, *ChemCatChem* 2015, 7, 2161-2178), rhenium-copper-carbon composites (U. G. Hong, J. K. Kim, J. Lee, J. K. Lee, J. H. Song, J. Yi, I. K. Song, *Appl. Catal. A Gen.* 2014, 469, 466-471), Pd/TiO$_2$ (B. Tapin, F. Epron, C. Especel, B. K. Ly, C. Pinel, D. Poitiers, U. De Poitiers, U. M. R. Cnrs, M. Brunet, *ACS Catal.* 2013, 3, 2327-2335), and Ru/C (R. M. Deshpande, V. V. Buwa, C. V. Rode, R. V. Chaudhari, P. L. Mills, *Catal. Commun.* 2002, 3, 269-274), have been utilized for aqueous-based BDO production at temperatures and H$_2$ pressures ranging from 160 to 240° C. and 80 to 150 bar, respectively. Examples of high selectivity (over 50%) for BDO were reported only at low temperatures (below 170° C.) and high H$_2$ pressures (over 140 bar). Presumably these conditions are necessary to overcome the entropically unfavorable ring-opening γ-butyrolactone with hydrogen to form BDO.

Comparatively fewer examples of IA or MA hydrogenation to MBDO exist in the literature. While MBDO has been produced in high yield (>90%) from either IA or MGBL using homogenous Ru-triphos catalysts (F. M. A. Geilen, B. Engendahl, A. Harwardt, W. Marquardt, *Angew. Chemie* 2010, 122, 5642-5646; and F. M. a Geilen, B. Engendahl, M. H, W. Leitner, *J. Am. Chem. Soc.* 2011, 14349-14358) and Ru complexes with tetradentate bipyridine ligands (W. Li, J. Xie, M. Yuan, Q. Zhou, *Green Chem.* 2014, 16, 4081-4085), heterogeneous catalysts have been explored with less success. Synthesis of MBDO from IA at moderate temperature and pressure produced low yield (45% at 150° C. and 100 bar) (R. Fischer, R. Pinkos, J. Wulff-Doring, *Method for Producing Aliphatic Alcohols*, 2001, U.S. Ser. No. 09/423, 876). Recently, Pd—Re/C has been reported as an effective catalyst under conditions of relatively high temperature and low $H_2$ pressure (>80% yield of MBDO at 180° C. and 40 bar) (X. Liu, X. Wang, Q. Liu, G. Xu, X. Li, X. Mu, *Catal. Today* 2016, DOI http://dx.doi.org/10.1016/j.cattod.2016.01.041) in conflict with the thermodynamics of the ring opening of the lactone to the diol, which should prevent higher yields of MBDO under these conditions. A number of catalysts, including Ru/Starbon (R. Luque, J. H. Clark, *Catal. Commun.* 2010, 11, 928-931), Ru/C (Q. Huang, W. Yu, R. Lu, F. Lu, J. Gao, H. Miao, J. Xu, RSC Adv. 2015, 5, 97256-97263), Ru/TiO$_2$ (A. Primo, P. Concepcióon, A. Corma, *Chem. Commun.* (Camb). 2011, 47, 3613-3615), and Pd/C have previously proven ineffective for the reduction of IA to MBDO in a one-pot approach (S. Li, X. Wang, X. Liu, G. Xu, S. Han, X. Mu, *Catal. Commun.* 2015, 61, 92-96).

Figure 1A:
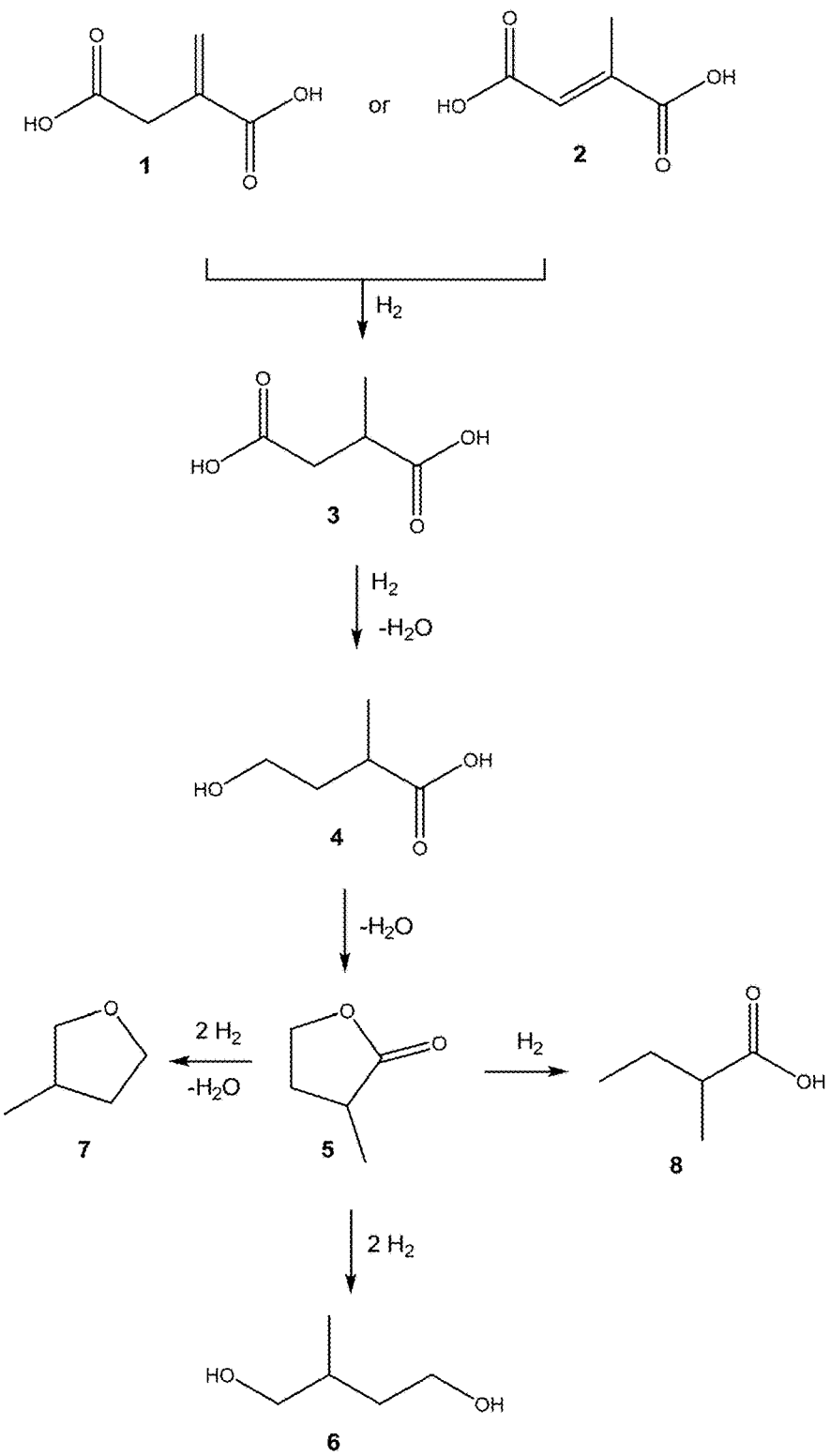
FIG. 1A shows a detailed pathway for the hydrogenation of itaconic acid (IA) (compound 1 in FIG. 1A) and mesaconic acid (MA) (compound 2 in FIG. 1A) to 2-methyl-1,4-butanediol MBDO.
Figure 17:
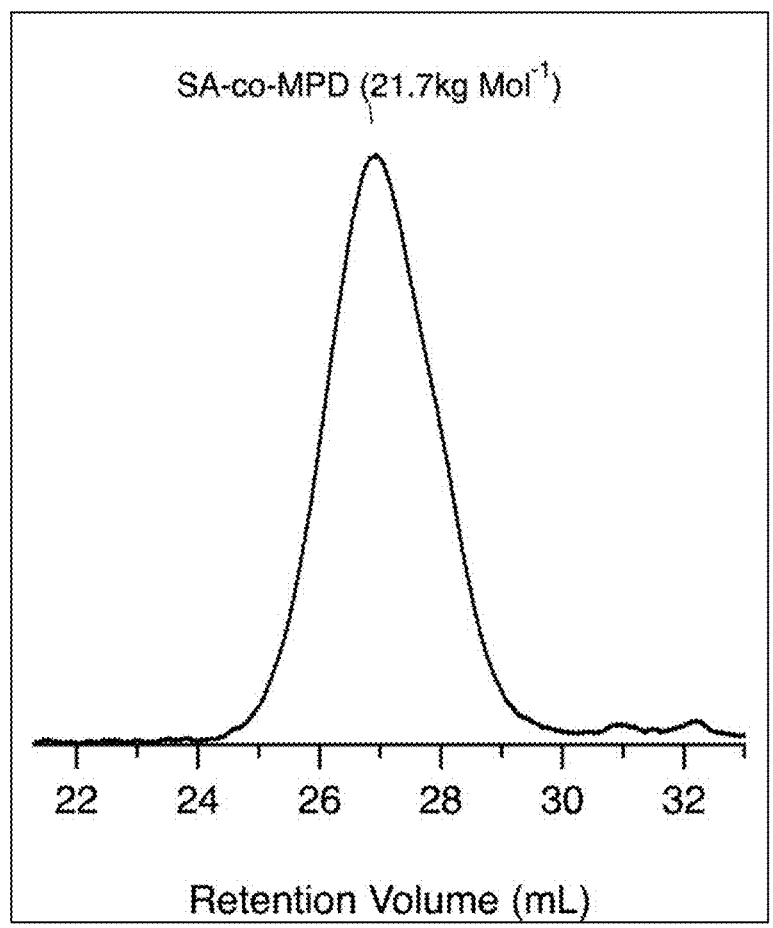
FIG. 17 shows a SEC Chromatograph (THF mobile phase) of PMPS.
Figure 18:
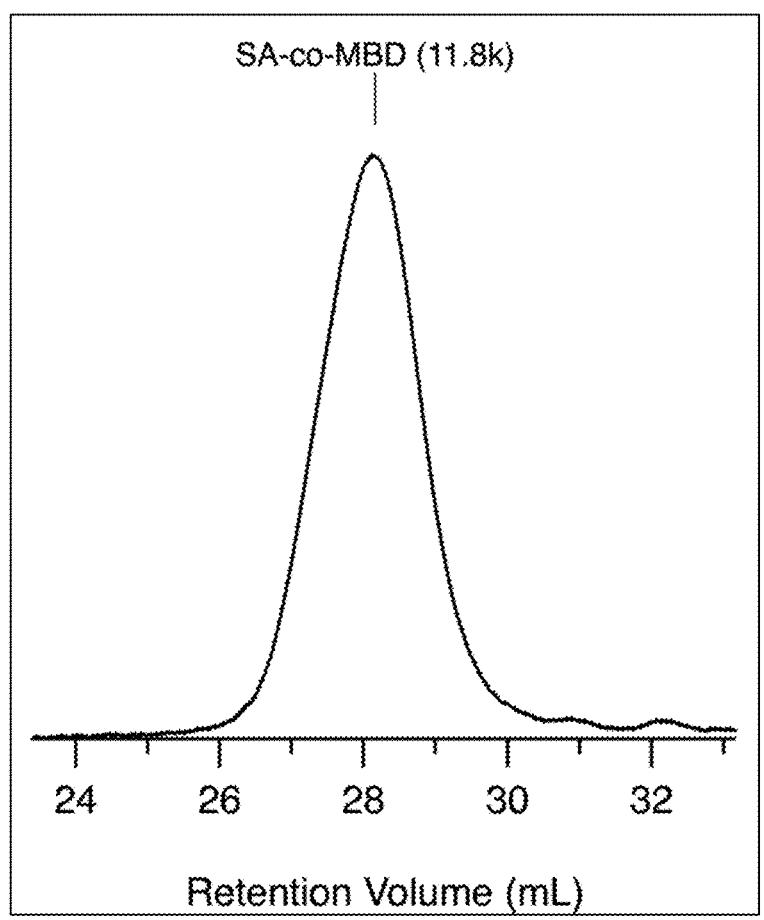
FIG. 18 shows a SEC Chromatograph (THF mobile phase) of PMBS.
Figure 19A:
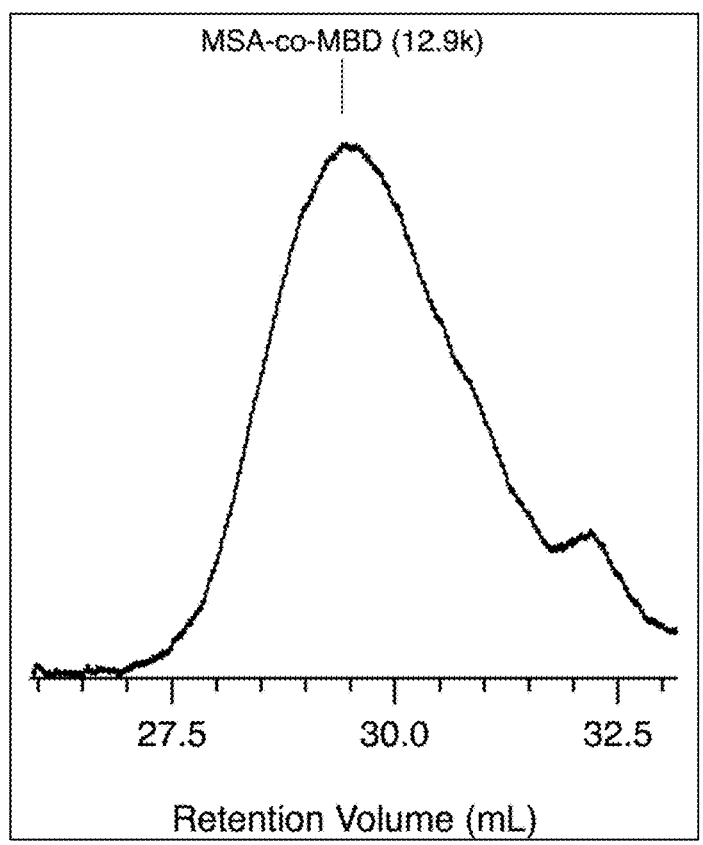
FIGS. 19A and 19B show SEC Chromatograph (THF mobile phase) of PMBMS-1 (FIG. 19A) and PMBMS-2 (FIG. 19B).
Figure 19B:
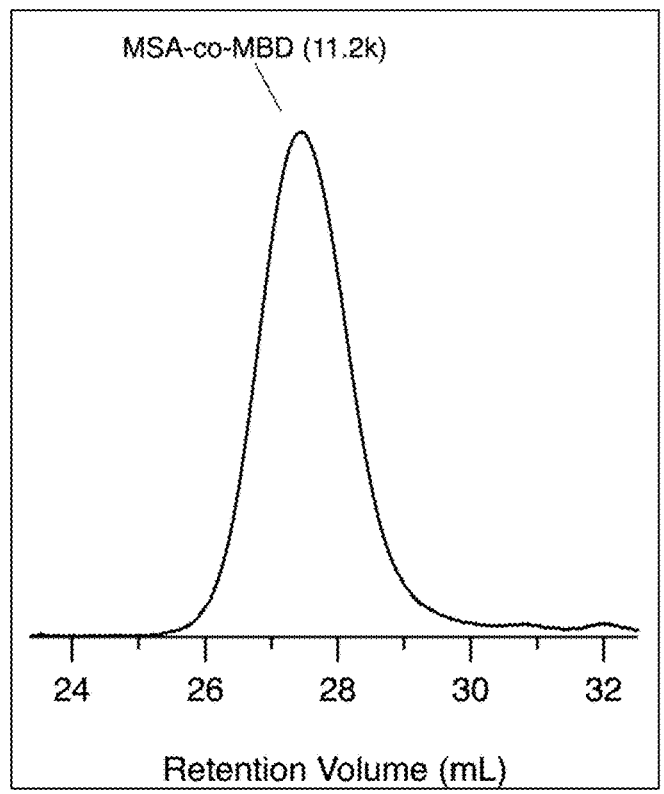

FIG. 1A shows a detailed pathway for the hydrogenation of IA (compound 1 in FIG. 1A) and MA (compound 2 in FIG. 1A) to MBDO (compound 6 in FIG. 1A). More specifically, FIG. 1A shows the reaction pathway for the hydrogenation of itaconic acid (1) and mesaconic acid (2) to 2-methyl-succinic acid (3), (2 or 3)-methyl-4-hydroxybutyric acid (4), (α or β)-methyl-γ-butyrolactone (5), and 2-methyl-1,4-butanediol (6). Side products include 3-methyl-tetrahydrofuran (7) and (2 or 3)-methyl-butyric acid (8). Note that the regioisomers of 4, 5, and 8 with alternate methyl positions are omitted from the drawing for clarity.

Thermodynamic calculations for the hydrogenation of IA and MA were performed to determine illustrative conditions that may produce MBDO with high selectivity. The result of these thermodynamic calculations can be seen in FIG. 1B. Specifically, FIG. 1B shows a calculated reaction energy diagram for the hydrogenation of itaconic acid (1) and mesaconic acid (2) to 2-methyl-1,4-butanediol (6) for three different sets of temperatures and pressures demonstrating high pressure and low temperature promote 6 formation. The inset of FIG. 1B shows theoretical temperature dependence (dashed line) and experimental overlay (markers) for the equilibrium [6]/([6]+[5]) ratio at $H_2$ pressure of 140 bar. Data in FIG. 1B is shown in the Examples in Table 2.

As expected, isomers IA and MA exhibit similar thermodynamic properties; hydrogenation to form 2-methyl-succinic acid (MSA) is highly favorable at all conditions. Subsequent reduction of the carbonyl to make (2 or 3)-methyl-4-hydroxybutyric acid (MHBA) followed by intramolecular esterification to form MGBL is also downhill in free energy, suggesting that MGBL is the thermodynamically-preferred product for all high temperature, high $H_2$ pressure conditions.

In contrast, conversion of MGBL to MBDO is unfavorable at high temperature and low pressure ($\Delta G_r$=3.5 kcal mol$^{-1}$ at 220° C. and 50 bar) but is favored at lower temperatures and higher pressures ($\Delta G_r$=−3.5 kcal mol$^{-1}$ at 80° C. and 200 bar). The theoretical temperature dependence of the ratio [MBDO]/([MBDO]+[MGBL]) at 140 bar of $H_2$ is displayed in the inset of FIG. 1B (dashed line). Experimental results obtained from 10 hydrogenation trials in which thermodynamic equilibrium between MGBL and MBDO was achieved generally agree with these theoretical predictions (markers, see Examples section below). Both theory and experiment show that low temperatures (<140° C.) are required to produce MBDO in high yield.

Pd/C has previously been demonstrated to be active for the conversion of IA to MGBL by Li et al. who examined the effects of active carbon pre-treatment on selectivity for MGBL formation (S. Li, X. Wang, X. Liu, G. Xu, S. Han, X. Mu, *Catal. Commun.* 2015, 61, 92-96). Here, we show the effect of temperature and pressure on the TOF for MGBL formation, demonstrating TOFs greater than 1000 h$^{-1}$ at 240° C. and 140 bar. It is thought, but not relied upon that the ability of palladium to incorporate hydrogen into its crystal lattice is possibly the reason for its superior performance relative to other tested catalysts. While Pd was highly active for both hydrogenation of double bond in IA or MA as well as the hydrogenation of the free carboxylic acid present in MSA, Pd/C did not catalyze the facile conversion of MGBL to MBDO. Studies of succinic acid hydrogenation using Pd-based catalysts found similar results, where low concentration of the diol was formed using Pd-only catalysts (B. Tapin, F. Epron, C. Especel, B. K. Ly, C. Pinel, D. Poitiers, U. De Poitiers, U. M. R. Cnrs, M. Brunet, *ACS Catal.* 2013, 3, 2327-2335).

Figure 3:
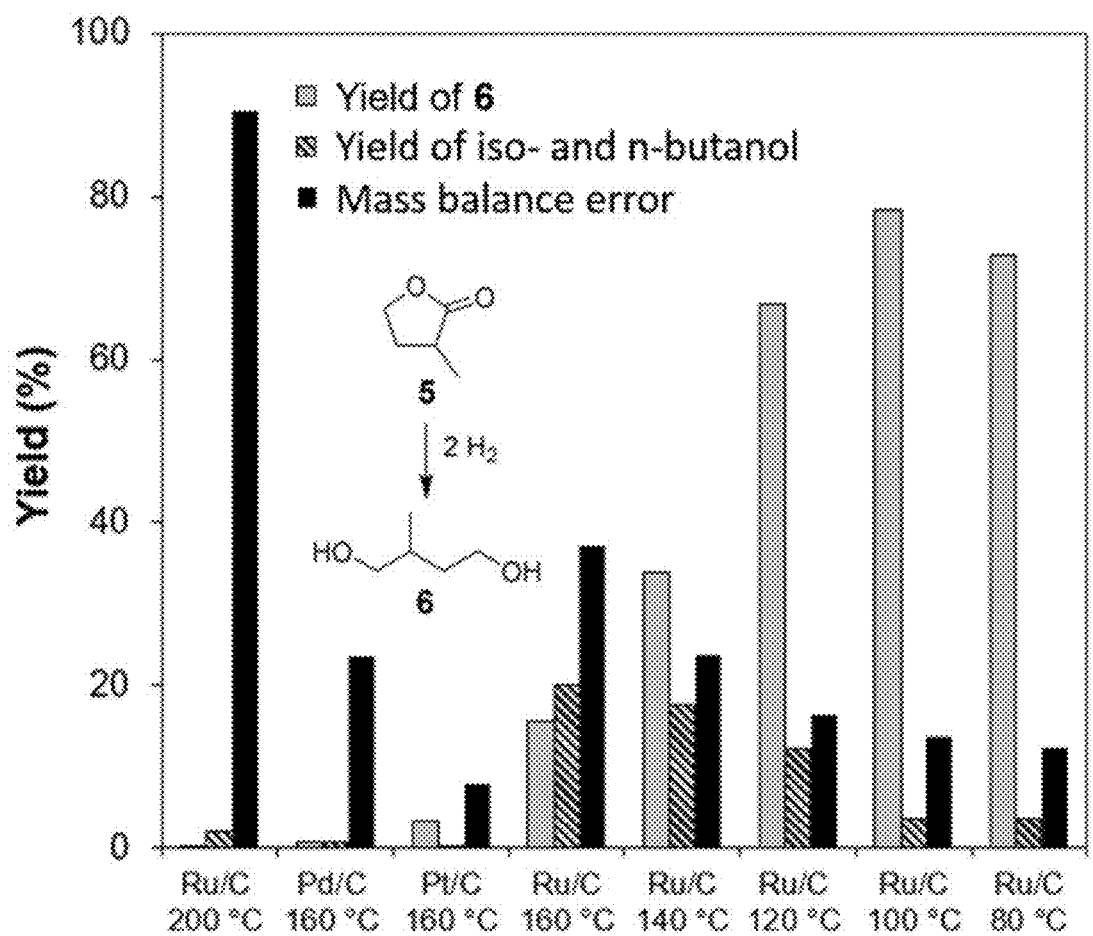
FIG. 3 shows the temperature dependence of hydrogenation of α-methyl-γ-butyrolactone to 2-methyl-1,4-butanediol. Reaction conditions: 2 wt. % MGBL in 60 mL $H_2O$, 1.0 g 5 wt. % Ru/C, 140 bar. Data reported at time of maximum MBDO selectivity: 80° C. (71 h—did not reach maximum), 100° C. (6.3 h), 120° C. (3.5 h), 140° C. (1.8 h), 160° C. (0.3 h), 200° C. (0.3 h). Pd/C (1.5 h), Pt/C (1.5 h).

Further, thermodynamic calculations indicated that at 140 bar, the conversion of MGBL to MBDO is only favorable at temperatures below ~140° C. (at higher $H_2$ pressures, the threshold temperature is higher); thus a low-temperature-active catalyst was required for the second step. Bimetallic catalysts composed of Pd—Re have been proposed for the conversion of closely-related γ-butyrolactone to BDO (D. P. Minh, M. Besson, C. Pinel, P. Fuertes, C. Petitjean, *Top. Catal.* 2010, 53, 1270-1273; B. K. Ly, D. P. Minh, C. Pinel, M. Besson, B. Tapin, F. Epron, C. Especel, *Top. Catal.* 2012, 55, 466-473; and B. K. Ly, B. Tapin, M. Aouine, P. Delichere, F. Epron, C. Pinel, C. Especel, M. Besson, *ChemCatChem* 2015, 7, 2161-2178). Disclosed herein, it was found that the monometallic Ru/C effectively promotes conversion of MGBL to about 80% yield of MBDO, as shown in FIG. 3. The rate of Ru leaching from Ru/C was sufficiently low, demonstrating process viability (i.e, the rate of leaching was three to four orders of magnitude lower than a viable rate J. W. Shabaker, D. A. Simonetti, R. D. Cortright, J. A. Dumesic, *J. Catal.* 2005, 231, 67-76)) and that the reaction was catalyzed heterogeneously (complete details in the examples below). While MBDO displays a similar reactivity to BDO, its branched C5 structure imparts a unique set of physical properties.

Previous work addressing the conversion of γ-valerolactone to 1,5-pentanediol with homogeneous Ru-based catalysts suggests that the intermediates for lactone hydrogenation to diols are the lactol and open chain hydroxylaldehyde; the remaining carbonyl is then hydrogenated to yield the diol (F. M. A. Geilen, B. Engendahl, A. Harwardt, W. Marquardt, *Angew. Chemie* 2010, 122, 5642-5646). It is apparent from that disclosed herein that Ru/C promotes C—O bond breaking necessary lactone ring opening. Re could also promote the ring-opening mechanism, given the results obtained with Re for succinic acid hydrogenation) Z. Shao, C. Li, X. Di, Z. Xiao, C. Liang, *Ind. Eng. Chem. Res.* 2014, 53, 9638-9645). The undesired hydrogenolysis of MBDO to isobutanol and n-butanol is also known; generically, $RCH_2OH+2H_2 \rightarrow RH+CH_4+H_2O$ (B. Wojcik, H. Adkins, *J. Am. Chem. Soc.* 1933, 55, 1293-1294; and R. M. Deshpande, V. V. Buwa, C. V. Rode, R. V. Chaudhari, P. L. Mills, *Catal. Commun.* 2002, 3, 269-274). For MBDO, the end products of hydrogenolysis are $C_3H_8+2CH_4+2H_2O$.

As disclosed herein, splitting the overall process into two sequential steps with monometallic catalysts affords high yields of MBDO. The initial step of a dicarboxylic acid, such as IA or MA for example, at relatively high temperatures (240° C.) produces high TOFs on Pd/C that stops at MGBL formation. If this first reaction was conducted with bimetallic catalysts that contain Re or Ru, then negligible ring opening of MGBL would occur since the thermodynamic equilibrium ratio of [MBDO]/([MBDO]+[MGBL]) is near zero at this temperature. The high temperature exacerbates the entropic penalty of combining MGBL and two hydrogen molecules to produce MBDO. Moreover, the high reaction temperature would lead to undesirable hydrogenolysis reactions of the little MBDO that was produced. A proposed pathway for the Ru-catalyzed hydrogenolysis over-conversion of 2-methyl-1,4-butanediol to propane and methane is shown below in Scheme 2.

Scheme 2

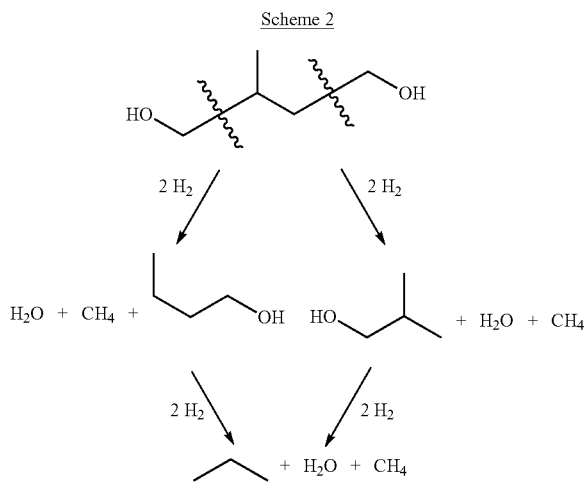

Conversely, a single low temperature for the entire reaction sequence would lead to negligibly slow overall rates that are limited by the conversion of IA to MGBL.

As discussed herein, biomass-derived feedstocks can be utilized in hybrid fermentation/thermocatalytic process to produce drop-in replacements or entirely new chemicals that extend into new applications (S. K. Green, R. E. Patet, N. Nikbin, C. L. Williams, C.-C. Chang, J. Yu, R. J. Gorte, S. Caratzoulas, W. Fan, D. G. Vlachos, et al., Appl. Catal. B Environ. 2016, 180, 487-496). Although MBDO, MPDO, and MPTO were previously too expensive for most commercial applications, the development of this efficient reduction method that utilizes inexpensive and abundant precursors (IA, MA, and MLA) will enable their low cost production and use.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one. Reference to "a carboxylic acid compound", for example, refers to a single carboxylic acid compound, multiple compounds of the same carboxylic acid compound, more than one specific carboxylic acid compound, multiple types of carboxylic acid compounds, mixtures of carboxylic acid compounds, or any combination thereof.

As used herein, "alkyl" is an unsubstituted or substituted saturated hydrocarbon chain radical having from 1 to about 12 carbon atoms; from 1 to about 10 carbon atoms; or from 1 to about 6 carbon atoms. Illustrative, non-limiting examples of alkyl groups include, for example, methyl, ethyl, propyl, iso-propyl, and butyl. A $C_2$ to $C_4$ substituted or unsubstituted alkyl radical, for example refers to a $C_2$ to $C_4$ linear alkyl chain that may be unsubstituted or substituted. If the $C_2$ to $C_4$ linear alkyl chain is substituted with an alkyl radical, the carbon number of the alkyl radical increases as a function of the number of carbons in the alkyl substituent.

As used herein, "alkenyl" is an unsubstituted or substituted hydrocarbon chain radical having from 2 to about 12 carbon atoms; from 2 to about 10 carbon atoms; or from 2 to about 6 carbon atoms. Alkenyls have at least one olefinic double bond. Illustrative, non-limiting examples of alkenyls include vinyl, allyl, and butenyl.

As used herein, "hydroxyl group" refers to a substituent group of formula —OH.

As used herein, "carboxylic acid group" refers to substituent group of formula —C(=O)OH.

As used herein, "lactone" refers to a cyclic ester containing a 1-oxacycloalkan-2-one portion.

Unless otherwise stated, as employed herein, when a moiety (e.g., alkyl, or alkenyl) is described as "substituted" it is meant that the group optionally has from one to four, from one to three, or one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order, unless context indicates otherwise. And, as appropriate, any combination of two or more steps may be conducted simultaneously.

All headings are for the convenience of the reader and should not be used to limit the meaning of the text that follows the heading, unless so specified.

EXAMPLES

The invention is illustrated by the following examples. It is to be understood that the particular examples, materials, amounts, and procedures are to be interpreted broadly in accordance with the scope and spirit of the disclosure as set forth herein.

Materials and Methods:

Catalysts: Pd/C (10 wt. % Pd on activated carbon), Pt/C (10 wt. % Pt on activated carbon), Ru/C (5 wt. % on carbon), $Cu_2Cr_2O_5$, and Ni on silica/alumina (65 wt. %) were purchased from Sigma Aldrich and used without pre-treatment. Polymerization catalysts titanium (IV) isopropoxide (97%, Aldrich), and tin(II) 2-ethylhexanoate (92.5-100%, Aldrich) were also used as received.

Reagents and Solvents: Itaconic acid (>99%, Sigma Aldrich), mesaconic acid (99% Sigma Aldrich), α-methyl-γ-butyrolactone (98% Sigma Aldrich), succinic acid (99%, Aldrich), Methyl-succinic acid (99%, Aldrich), 3-Methyl-1, 5-pentane diol (TCI America), Toluene (>99.5%, Fisher), Methanol (>99.8, Fisher) were used without purification.

Pd/TiO$_2$ was synthesized according a method previously described in the literature (B. K. Ly, D. P. Minh, C. Pinel, M. Besson, B. Tapin, F. Epron, C. Especel, *Top. Catal.* 2012, 55, 466-473). Briefly, 0.63 g potassium tetrachloropalladate was added to a suspension of 10 g TiO$_2$ (Cristal Activ DT-51, 90 m$^2$/g) to achieve 2 wt. % Pd/TiO$_2$. The mixture was stirred at room temperature for 30 min prior to the addition of KOH to obtain a pH of 11. The suspension was refluxed for 1 h, cooled, washed with excess water, dried under vacuum, and reduced in flowing H$_2$ at 300° C. for 3 h. et GC standards: methylsuccinic acid (99%, Sigma Aldrich), s-2-methyl-1,4-butanediol (>97% Sigma Aldrich), 2-methylbutyric acid (98% Sigma Aldrich), 1-butanol (>99% Sigma Aldrich), 2-methyl-1-propanol (>99% Sigma Aldrich) were used as received.

Thermodynamic Calculations

Thermodynamic calculations were performed with the Gaussian 09 (Rev A.2) program (Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenb, D. J. *Gaussian* 09 (Rev. A.2); Gaussian, Inc. Wallingford, Conn., 2009) using the M062X/6-311++G(3df,3pd) level of theory and the SMD model (Marenich, A. V.; Cramer, C. J.; Truhlar, D. G. *J. Phys. Chem. B* 2009, 113(18), 6378-6396) with water as the solvent. The temperature- and pressure-dependence of the Gibbs free energy was calculated using the standard thermochemistry equations used within the Gaussian program (Ochterski, J. W. Gaussian Inc, Pittsburgh, Pa. 2000, 1-17). These equations use the contributions from translational motion, electronic motion, rotational motion, and vibrational motion to correct the Gibbs free energy at zero Kelvin for any given temperature (T) and pressure (P). Translational motion is dependent on both T and P, while electronic, rotational, and vibrational motions are only a function of T. All molecules are assumed to be non-interacting, ideal gases.

A complete description of entropy calculation is described in the literature (Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenb, D. J. *Gaussian* 09 (*Rev. A.2*); Gaussian, Inc. Wallingford, Conn., 2009). The translational partition function and the equation for the translational partition function and entropy is shown below, to illustrate the effect of pressure on entropy (and ultimately Gibbs free energy), $$q_t = \left(\frac{2\pi m k_B T}{h^2}\right)^{3/2} \frac{k_B T}{P} \tag{S5}$$

$$S_t = R\left(\ln(q_t e) + T\left(\frac{3}{2T}\right)\right) \tag{S6}$$

In equation (S6), P is pressure. As pressure increases, the entropy per molecule decreases and thus the Gibbs free energy (H−TS) per molecule increases. For a reaction in which three molecules are converted to 1 (i.e., MGBL+ 2H$_2$→MBDO), the net effect is that the Gibbs free energy of the reaction decreases with increasing pressure. For this reaction, temperature has the opposite effect. Since the change in entropy of the reaction is negative, increasing temperature increases the Gibbs free energy of reaction. Thus, the reaction above is favored at low temperature and high pressure.

The Gibbs free energies of reaction (ΔG) presented in FIG. 1B were calculated by subtracting the sum of the Gibbs free energies of the reactants from the products for each step of the reaction sequence, $$\Delta G(T,P) = \Sigma_{products} G(T,P) - \Sigma_{reactants} G(T,P) \tag{S7}$$

In equation S7 the reactants were MA (C$_5$H$_6$O$_4$)+5H$_2$, and the products were MSA (C$_5$H$_8$O$_4$)+4H$_2$, MHBA (C$_5$H$_{10}$O$_3$)+2H$_2$+H$_2$O, MGBL (C$_5$H$_8$O$_2$)+2H$_2$+2 H$_2$O, and MBDO (C$_5$H$_{12}$O$_2$)+2H$_2$O for the first, second, third, and fourth reaction steps, respectively. The total number of carbon (5), hydrogen (16), and oxygen (4) atoms were thus conserved throughout the reaction scheme.

The temperature-dependence of the equilibrium concentrations of MBDO and MGBL was evaluated from the equilibrium constant (K), calculated from the delta Gibbs free energy of reaction, −ΔG$_r$(T,P) for the reaction of MGBL→MBDO+2H$_2$, $$K = e^{\frac{-\Delta G_r(T,P)}{RT}} \tag{S8}$$

where R is the universal gas constant and T is temperature. K is related to the activities of MBDO and MGBL through the relationship $$K = \frac{a_{MBDO}}{a_{MGBL} a_{H_2}^2} \tag{S9}$$

where $\alpha_i$ refers to the activity of component i in solution. The activity of hydrogen in the gas phase is equal to the hydrogen pressure divided by the reference pressure of the calculations (which is equal to the total pressure of the system, as accounted for in the calculations). Because the total pressure of the system was dominated by the pressure of hydrogen at the relevant reaction temperatures (e.g., the water vapor pressure is less than 5% of the total pressure at 160° C. and 140 bar H$_2$), the activity of hydrogen is approximately one. By definition, the activity of hydrogen in the liquid phase is equal to the activity of hydrogen in the gas phase; thus the liquid phase activity of hydrogen is one. The ratio of the activities of MBDO and MGBL is equal to the ratio in molar concentrations, assuming an ideal solution. Thus, equation (S9) simplifies to $$K = \frac{[MBDO]}{[MGBL]} = e^{\frac{-\Delta G_r(T,P)}{RT}} \tag{S10}$$

where [MBDO] and [MGBL] refer to the molar concentrations of MBDO and MGBL, respectively. Solving this equation for the equilibrium ratio of MBDO (MBDO$_{,eq}$) gives, $$MBDO_{,eq} = \frac{[MBDO]}{[MGBL]+[MBDO]} = \frac{e^{\frac{-\Delta G_r(T,P)}{RT}}}{1+e^{\frac{-\Delta G_r(T,P)}{RT}}}. \quad (S11)$$

Equation (S11) was used to plot the dotted line in the inset of FIG. 1B using the temperature- and pressure-dependent Gibbs free energy of reaction data from the Gaussian 09 calculations.

Synthesis Methods

Synthesis of 4-methyltetrahydro-2H-pyran-2-one (β1)

4-methyltetrahydro-2H-pyran-2-one (β1) was synthesized using the method of Longley et al (Longley, R. I.; Emerson, W. S. (β-Methyl-δ-Valerolactone *Organic Synthesis Coll.* 1963, 4, 677). In a 3 L round bottomed flask fitted with a thermometer, reflux condenser, and bubbler 3-methyl-1,5-pentanediol (2L, 16.9 moles) and copper chromite (100 grams) were stirred and heated to 200° C. until hydrogen evolution slowed (~12 hours). The reaction was then cooled and β1 (1700 grams, 85% yield) was removed by reduced pressure distillation directly from the reaction flask. The crude product was further purified by repeated distillation from calcium hydride.

Synthesis of Anhydromevalonate:

Anhydromevalonolactone was produced from mevalonate using the methods previously described (M. Xiong, D. K. Schneiderman, F. S. Bates, M. A. Hillmyer, K. Zhang, *Proc. Natl. Acad. Sci.* 2014, 111, 8357-8362). The mevalonate fermentation broth (containing 28 g L$^{-1}$ mevalonate as determined by HPLC) was filtered through activated charcoal to remove cell debris and colored impurities. Then concentrated H$_2$SO$_4$ (200 ml) was slowly charged into the filtered fermentation broth (2 L) under vigorous stirring. The acid solution was refluxed for 15 h, then cooled and extracted with chloroform. The chloroform was removed under reduced pressure and the crude product distilled to yield pure AMVL (39 grams, 82% gravimetric yield).

Synthesis of Mevalonolactone:

The fermentation broth (containing 28 g L$^{-1}$ mevalonate as determined by HPLC) was filtered through activated charcoal to remove cell debris and colored impurities. The water was removed under reduced pressure, and then the mevalonolactone was then taken up into acetone, dried over magnesium sulfate, filtered, and concentrated under reduced pressure.

Instrumental Methods $^1$H NMR Spectroscopy:

$^1$H NMR spectra were collected from CDCl$_3$ solution on a Varian INOVA-500 spectrometer operating at 500 MHz. Chemical shifts are referenced to the protic solvent peaks at 7.26 ppm. $^1$H NMR spectra of polymer samples are reported as the average of at least 16 scans and were acquired using a 5 second acquisition time and a 10 second delay.

Elemental Analysis.

Leaching of the solid catalysts into solution was measured on a ICP-MS (Thermo Scientific XSERIES 2 ICP-MS with ESI PC3 Peltier cooled spray chamber, SC-FAST injection loop, and SC-4 autosampler). Samples for ICP-MS were diluted appropriately and 40 ppb of indium internal standard was added. Elements were analyzed using He/H$_2$ collision-reaction mode. The aqueous filtrate from the reaction MGBL to MBDO with the highest yield at 100° C. was tested by ICP-MS. 16.2 ppb of Ru was present in the 60 mL reaction volume (after 23 h at 100° C.) which equates to 1.95×10$^{-5}$% of the initial Ru added to the reactor. Based on this rate, it was estimated that >65 yrs of continuous operation at 100° C. is required for 50% of the Ru to leach into solution.

Metal Dispersion.

Metal dispersions for Pd/TiO$_2$ and Pd/C were determined using a Quantachrome ChemBET Pulsar TPR/TPD Automated Chemisorption Analyzer. 0.5 g of sample was loaded into a U-shaped quartz tube. Samples were reduced at 250° C. under flowing hydrogen for 1 h, purged at 250° C. under flowing helium for 1 h, and cooled to 35° C. for analysis. CO chemisorption was performed by sequential 282.5 µL injections of pure CO until saturation of metal surface sites. Pd dispersion was calculated assuming a 1:1 stoichiometry of adsorbed CO to surface Pd atoms.

Differential Scanning Calorimetry:

Differential scanning calorimetry was conducted on a TA Instruments Q-1000 DSC under nitrogen. Samples were analyzed in hermetically sealed aluminum pans. To ensure consistent thermal history the samples were first equilibrated at −80° C. then heated to 150 at 10° C. min$^{-1}$. Following this the sample was cooled to −80 at 10° C. min$^{-1}$, then reheated to 150° C. at the same rate. All glass transitions reported in this work were found upon the second heating cycle and are taken as the inflection point Size Exclusion Chromatography:

Dispersity and mass-average molar mass were determined using a size exclusion chromatography instrument with THF as the mobile phase at 25° C. and a flow rate of 1 mL min$^{-1}$. Size exclusion was performed with three successive Phenomenex Phenogel-5 columns. Chromatograms were collected using a Wyatt Technology DAWN DSP MALLS detector and a Wyatt optilab EX RI detector. The dn/dc values polymer samples were estimated using size exclusion chromatography with samples of known concentration in THF. This indirect ("in-line") method uses the total area of the RI signal and the assumption of 100% of the sample mass is recovered to calculate dn/dc. Molar mass characteristics of the poly(1,4-butanediol-co-succinic acid) (PBS) sample were analyzed using size exclusion chromatography in chloroform at 35° C. on a Hewlett-Packard 1100 series liquid chromatograph (Palo Alto, Calif.) equipped with three PLgel 5 mm Mixed-C columns in series with the molecular weight range of 400-400000 g mol$^{-1}$. A Hewlett-Packard 1047A refractive index detector was employed. The molecular weights and dispersity (Đ) of the polymers were calculated relative to linear polystyrene standards from Varian, Inc. (Palo Alto, Calif.).

Thermogravimetric Analysis (TGA):

TGA was performed on a TA Instruments Q500 under nitrogen atmosphere at a heating rate of 10° C./min with typical sample size of 10-15 mg.

Hydrogenation Reactions:

Reduction Reactions were performed in 100 mL high pressure reactors (model 4598HPHT, Parr Instrument Co.) equipped with Hastelloy C-276 internals, a magnetic stirrer with gas-entrainment propeller, liquid sampling port, and electronic pressure gauge. Polymerization reactions were conducted in round bottom flasks equipped with a magnetic stirrer and gas adapter. Round bottom flasks, Teflon stir bars, and gas adaptors used for polymer synthesis were dried in a 110° C. oven for a minimum of 12 hours prior to use.

Hydrogenation of IA or MA:

Hydrogenation of IA or MA: In a representative hydrogenation of itaconic acid, 6 g of itaconic acid was added to 54 mL of deionized water. The mixture was added to the reaction cylinder along with 1 g of Pd/C powder. The solution was stirred briefly prior to assembling on the reactor head. The reactor was purged with 100 bar nitrogen prior to filling with hydrogen and the magnetic stirrer was kept at a constant 1000 rpm. For a reaction at 140 bar, the reactor was pressurized initially to 100 bar, heated to the reactor temperature, and re-pressurized to 140 bar after temperature stabilization. Samples were obtained from the liquid sampling port by first purging the sample port followed by obtainment of a sample. The reactor was re-pressurized after each sample. 1,4-butanediol (BDO) was used as an internal standard whereby 400 µL of 0.2 wt. % BDO was added to 400 µL of each sample acquired from the reactor.

Hydrogenation of αMGBL:

In a representative hydrogenation of α-methyl-γ-butyrolactone, 1136 µL (1.2 g) of αMGBL was added to 59 mL deionized water. The mixture was added to the reaction cylinder along with 1 g Ru/C. Subsequent procedures were equivalent to those described above.

Hydrogenation of Anhydromevalonate:

1 mL of anhydromevalonate was added to 59 mL deionized water. The mixture was added to the reaction cylinder along with 0.5 g Ru/C. Subsequent procedures were equivalent to those described above.

Hydrogenation of β-methyl-γ-valerolactone 1 mL of β-methyl-γ-valerolactone was added to 59 mL deionized water. The mixture was added to the reaction cylinder along with 0.5 g Ru/C. Subsequent procedures were equivalent to those described above.

Hydrogenation of Mevalonolactone:

1 mL of mevalonolactone was added to 59 mL deionized water. The mixture was added to the reaction cylinder along with 1.0 g Ru/C. Subsequent procedures were equivalent to those described above.

Quantification was performed using a gas chromatograph (Agilent 7890) equipped with a catalytic microreactor-FID (Polyarc™, Activated Research Company, Eden Prairie, Minn.). The Polyarc™ reactor eliminates the need for detector calibration by converting all organic molecules to methane at the exit of the GC column, providing an equivalent response (on a per-carbon-atom basis) for every compound. The GC was configured as follows: liner: Agilent 5190-2295; column: Agilent DB-5, 0.32 mm ID, 0.25 µm film thickness; injection mode: 100:1 split; column flow rate: 2.5 std. $cm^3$ $min^{-1}$ He.

Example 1: Hydrogenation of IA or MA to MGBL

Figure 2:
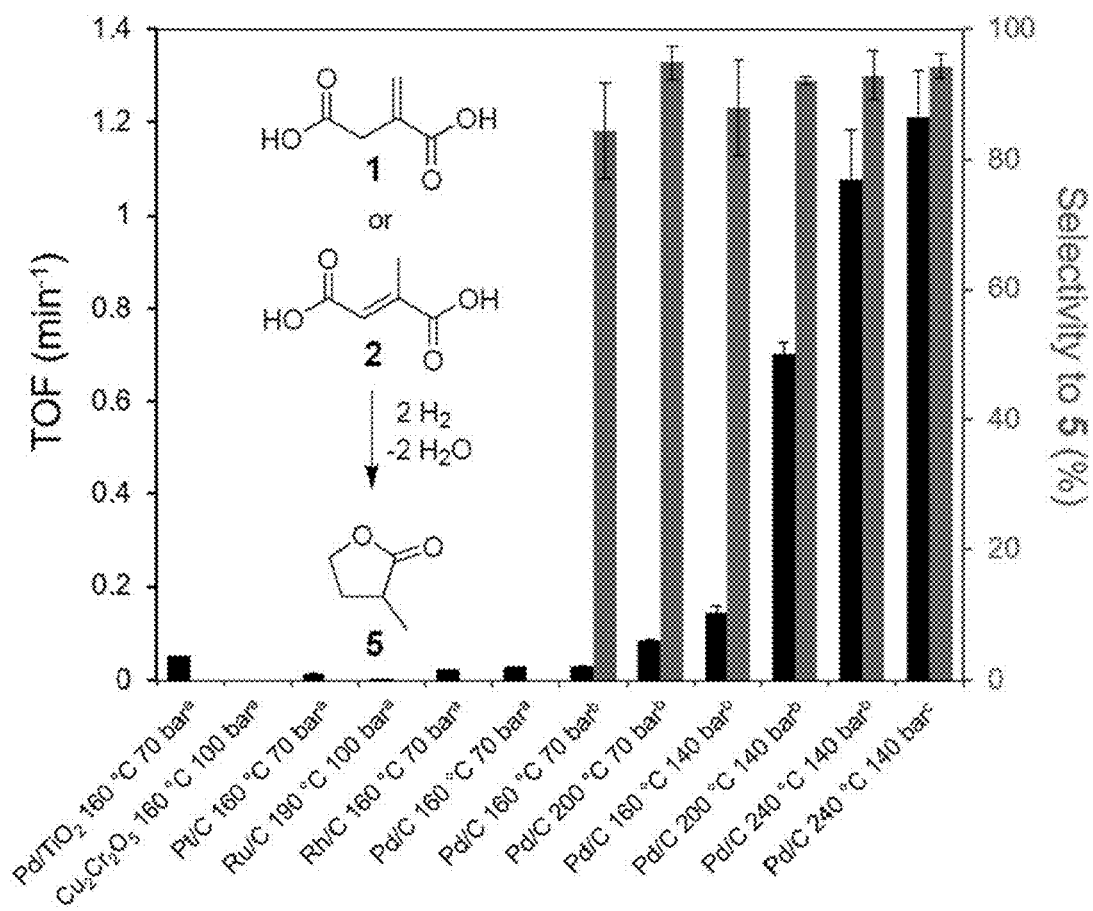
FIG. 2 shows the temperature and pressure dependence of itaconic acid conversion to α-methyl-γ-butyrolactone. Reaction conditions indicated by superscript where (a) 2 wt. % MA in $H_2O$, (b) 10 wt. % IA in $H_2O$, (c) 10 wt. % MA in $H_2O$. Total volume: 60 mL aqueous solution.

Experimental results for the aqueous hydrogenation of IA or MA to MGBL using heterogeneous catalysts are shown in FIG. 2. For the tested conditions, hydrogenation of IA or MA to form MSA was faster than the reduction and cyclization of MSA to MGBL. The rate of formation of MSA could not be quantified, since complete conversion was quickly obtained during initial reactor heating (~20 min).

TOF is defined as the rate of MBGL formation [mol MGBL $min^{-1}$] divided by the moles of surface metal atoms. The calculation of TOF and selectivity to MGBL (5) for data presented in FIG. 2 was calculated as:

$$\text{Selectivity to } MGBL = \frac{[MGBL]}{[MGBL] + [\text{by-products}]}$$

$$TOF = \frac{\text{rate of } MGBL \text{ formation}\left(\frac{mol}{min}\right)}{\text{total mol surface metal sites}}$$

where the byproducts quantified include (2 or 3)-methylbutyric acid, 3-methyltetrahydrofuran, (2 or 3)-methyl-1-butanol, isobutyric acid, and butyric acid.

As indicated by the turnover frequency (TOF) reported in FIG. 2, the rate of MGBL formation was dependent on catalyst and temperature. Pd catalysts exhibited higher TOFs than Pt, Ru, $Cu_2Cr_2O_5$, and Rh. At 160° C. and 70 bar $H_2$, Pd/$TiO_2$ and Pd/C demonstrate similar activity More specifically, FIG. 2 shows the temperature and pressure dependence of itaconic acid conversion to α-methyl-γ-butyrolactone. Reaction conditions indicated by superscript where (a) 2 wt. % MA in $H_2O$, (b) 10 wt. % IA in $H_2O$, (c) 10 wt. % MA in $H_2O$. Total volume: 60 mL aqueous solution. Complete reaction details provided in the Table 1, below. Selectivity is only reported for reaction conditions (a) and (b). MGBL is mixture of α-methyl-γ-butyrolactone and β-methyl-γ-butyrolactone (38±2% and 62±2%, respectively). Error bars represent a 95% confidence interval.

TABLE 1

Experimental information for the temperature and pressure dependence of the selectivity and activity of different catalysts for the reduction of mesaconic or itaconic acid to MGBL (presented in FIG. 2).

| Catalyst | Catalyst amount (g) | Temperature (° C.) | Pressure (bar) | TOF ($min^{-1}$)[d] | MGBL Selectivity (%) |
|---|---|---|---|---|---|
| Pd/$TiO_2$[a] | 0.50 | 160 | 70 | 0.050[e] | |
| $Cu_2Cr_2O_5$[a] | 0.15 | 160 | 100 | 0.000[e] | |
| Pt/C[a] | 0.50 | 160 | 70 | 0.013[e] | |
| Ru/C[a] | 0.25 | 190 | 100 | 0.003[e] | |
| Rh/C[a] | 0.15 | 160 | 70 | 0.022[e] | |
| Pd/C[a] | 1.0 | 160 | 70 | 0.029[e] | |
| Pd/C[b] | 1.2 | 160 | 70 | 0.028 ± 0.007 | 84.4 ± 7.4 |
| Pd/C[b] | 1.2 | 200 | 70 | 0.085 ± 0.005 | 94.8 ± 2.6 |
| Pd/C[b] | 1.2 | 160 | 140 | 0.14 ± 0.03 | 87.9 ± 7.3 |
| Pd/C[b] | 1.2 | 200 | 140 | 0.70 ± 0.05 | 92.1 ± 0.5 |
| Pd/C[b] | 1.2 | 240 | 140 | 1.1 ± 0.2 | 92.9 ± 3.7 |
| Pd/C[c] | 1.2 | 240 | 140 | 1.2 ± 0.2 | 94.3 ± 1.8 |

[a]Reaction conditions: 1.2 g MA in 60 mL DI $H_2O$.
[b]Reaction conditions: 6 g IA in 54 mL DI $H_2O$.
[c]Reaction conditions: 6 g MA in 54 mL DI $H_2O$.
[d]Catalyst dispersions used for calculation of TOF: Pd/$TiO_2$: 0.45, Pd/C: 0.18. Dispersion of Pt/C, Ru/C, and Rh/C approximated as 0.18.
[e]TOF determined from single data point, so there is no estimate of error.

Further optimization was performed with the commercial catalyst, Pd/C. With this catalyst, increasing the reaction temperature and pressure from 160° C. and 70 bar to 240° C. and 140 bar resulted in a 40-fold increase in TOF. The intermediate hydroxyacid, MHBA, was observed in small quantities (<5%) in reactions achieving high conversion to MGBL. Selectivity to MGBL was greater than 80% in all reactions using Pd/C. Thermodynamic calculations indicate that (2 or 3)-methylbutyric acid (MBA) formation from MGBL is a highly favorable reaction (ΔG=−17.6 kcal $mol^{-1}$ at 240° C. and 140 bar). The targeted diol, MBDO, was not observed in these experiments.

Subsequent conversion of MGBL to MBDO was tested with Ru/C, Pd/C, and Pt/C at temperatures ranging from 80° C. to 200° C. (FIG. 3). More specifically, FIG. 3 shows the temperature dependence of hydrogenation of α-methyl-γ-butyrolactone to 2-methyl-1,4-butanediol. Reaction conditions: 2 wt. % MGBL in 60 mL $H_2O$, 1.0 g 5 wt. % Ru/C, 140 bar. Data reported at time of maximum MBDO selectivity: 80° C. (71 h—did not reach maximum), 100° C. (6.3 h), 120° C. (3.5 h), 140° C. (1.8 h), 160° C. (0.3 h), 200° C. (0.3 h). Pd/C (1.5 h), Pt/C (1.5 h). TOF data is not presented for this reaction due to (1) the equilibrium that exists between MGBL and MBDO and (2) the hydrogenolysis of MBDO that occurs readily at temperatures greater than 100° C.

Pd and Pt produced low yields of MBDO, in contrast with Ru/C. Since conversion of MBDO to isobutanol, n-butanol, and ultimately propane, can occur in series with the formation of MBDO from MGBL, the data in FIG. 3 are presented at the time of maximum MBDO yield. With Ru/C at long reaction times, hydrogenolysis of the MBDO alkoxy C—C bonds occurs, resulting in the formation of methane and propane. Observed mass balance errors can presumably be attributed to the formation of these gaseous products, as only products in the aqueous phase were quantified. To maximize MBDO production it was necessary to conduct the MGBL reduction reactions at low temperatures where both the rate of MBDO hydrogenolysis was lower and the production of MBDO from MGBL was thermodynamically favorable. For example, the experimentally observed values for the ratio of [MBDO]/([MBDO]+[MGBL]) were 0.98 and 0.10 at 100° C. and 200° C., respectively, with Ru/C Calculation of yields and mass balance error for data presented in FIG. 3:

$$\text{Yield of } 6 = \frac{[6]_f}{[5]_i}$$

$$\text{Yield of iso- and n-butanol} = \frac{[\text{iso- and n-butanol}]_f}{[5]_i}$$

$$\text{Mass balance error} = 1 - \frac{[5]_f + [6]_f + [\text{iso- and n-butanol}]_f}{[5]_i}$$

Figure 4:
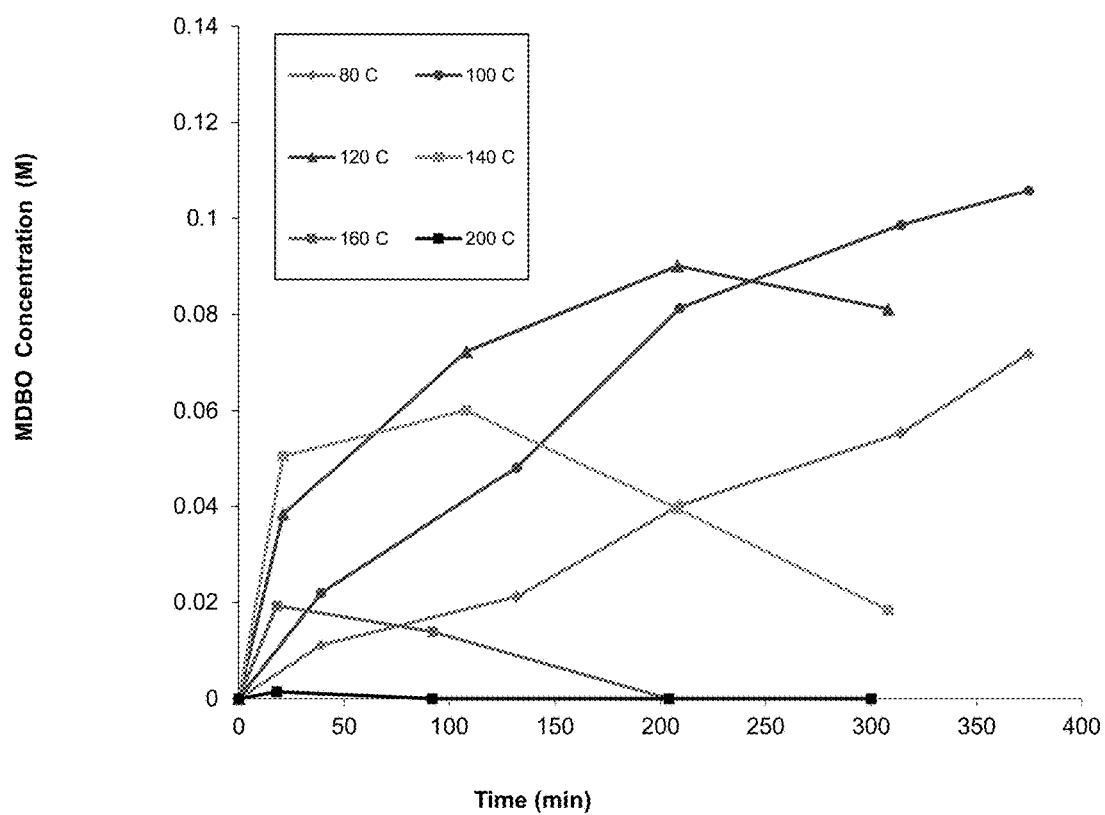
FIG. 4 shows concentration-time plots for the production of MDBO from MGBL for Ru/C.

FIG. 4 shows concentration-time plots for the production of MDBO from MGBL for Ru/C.

Example 2: Reduction of Mevalonolactone, Anhydromevalonate and β-Methyl-δ-valerolactone The reduction of three $C_6$ compounds: mevalonolactone (in water this molecule is in equilibrium with MLA), anhydromevalonate (AMLL), and β-Methyl-δ-valerolactone was investigated. Using conditions similar to those used for the reduction of MGBL (100° C., 140 bar $H_2$), it was found that the reduction of mevalonolactone resulted in 3-Methyl-1,3,5-pentanetriol (MPT) in high selectivity (91%). Additionally, the reduction of MLA and AMLL both gave 3-methyl-1,5-pentanediol (MPDO) with similarly high selectivity (86% to 91%).

Table 2 below shows data from this example.

TABLE 2

Catalytic data for the hydrogenation of mevalonic acid derivatives.

| Reactant | Product | Selectivity (%)[a] | Time (h) |
|---|---|---|---|
| Anhydromevalonate | 3-methyl-1,5-pentanediol | 89 | 16 |
| β-methyl-δ-valerolactone | 3-methyl-1,5-pentanediol | 86 | 16 |
| Mevalonolactone | 3-methyl-1,3,5-pentanetriol | 91 | 3.5 |

Reaction conditions: 1.0 g reactant, 1.0 g Ru/C, 59 mL DI $H_2O$, 100° C., 140 bar
[a]Selectivity defined as product molar concentration divided by total molar concentration of product and byproducts determined by GC.

Table 3 shows reaction conditions (reactant, catalyst(s), temperature) utilized in determining the temperature dependence of the equilibrium ratio of [MBDO]/([MGBL]+[MBDO]) at 140 bar (presented in FIG. 1B).

TABLE 3

Experimental information for the temperature dependence of the equilibrium ratio of [MBDO]/([MGBL] + [MBDO]) at 140 bar (presented in FIG. 1B).

| Entry | Reactant | Catalyst(s) | Temperature (° C.) | $MBDO,_{eq}$[d] | Time (h) |
|---|---|---|---|---|---|
| 1 | αMGBL[a] | 1.0 g Ru/C | 100 | 0.98 | 6.3 |
| 2 | αMGBL[a] | 1.0 g Ru/C | 120 | 0.99 | 3.5 |
| 3 | αMGBL[a] | 1.0 g Ru/C | 140 | 0.96 | 1.8 |
| 4 | αMGBL[a] | 1.0 g Ru/C | 160 | 0.43 | 0.3 |
| 5 | αMGBL[a] | 1.0 g Ru/C | 200 | 0.098 | 0.3 |
| 6 | MA[b] | 0.5 g Pd/SiO$_2$, 0.5 g Pd/C, 0.5 g Pt/C, 0.5 g Ni/SiO$_2$, 0.5 g Ru/C | 160 | 0.54 | 22 |
| 7 | MA[b] | 0.5 g Pd/SiO$_2$, 0.5 g Pd/C, 0.5 g Pt/C, 0.5 g Ru/C | 160 | 0.64 | 23 |
| 8 | MA[b] | 1.0 g Pd/SiO$_2$, 1.0 g Ru/C | 160 | 0.54 | 22.5 |
| 9 | MA[b] | 1.0 g Pd/C, 0.5 g Ru/C | 130 | 0.90 | 22 |
| 10 | αMGBL[c] | 2.0 g Ru/C | 100 | 0.96 | 8.3 |

[a]1.2 g αMGBL in 60 mL DI water.
[b]12 g MA in 60 mL DI water.
[c]0.93 g αMGBL in 60 mL DI water.
[d]MBDO,eq defined as [MBDO]/([MBDO] + [MGBL]).

In addition to BDO and MBDO, anhydromevalonolactone can be converted MPDO, a drop-in replacement monomer in the synthesis of specialty resins ("Industrial alcohols, diols," can be found under http://www.kuraray.co.jp/en/products/chemical/diols.html, 2016). Similarly, the reduction of mevalonate to produce 3-methyl-1,3,5-pentanetriol (MPTO), a C6 polyol qualitatively similar to glycerol has also been demonstrated and disclosed herein.

Example 3: Synthesis of Polymers

With several bio-based alcohols available, a variety of polyesters were produced using condensation polymerization with tin(II) 2-ethylhexanoate as a catalyst. As described below, MBDO was reacted with either SA or MSA to prepare each of the six possible polyester copolymers. As summarized in FIG. 5, the addition of a methyl substituent to either the diacid or diol had a dramatic impact on the thermal properties of the resulting polyester (K. W. Doak, H. N. Campbell, *J. Polym. Sci.* 1955, 18, 215-226; and A. J. B. Loman, D. E. R. Van Leen Does, A. Bantjes, I. Vulic, *J.*

Polym. Sci. Part A Polym. Chem. 1995, 33, 493-504). Whereas polybutylene succinate, the polymer resulting from the polymerization of succinic acid and 1,4-butanediol is semicrystalline with a melting point ($T_m$=114° C.), the methyl-substituted polyesters were all fully amorphous with low glass transition temperature values ($T_g$ below −35° C. for each sample). These soft and rubbery polyesters may be appropriate for numerous applications including use in coatings, adhesives, sealants, elastomers, and, foams (D. V Palaskar, A. Boyer, E. Cloutet, C. Alfos, H. Cramail, *Biomacromolecules* 2010, 11, 1202-1211; and D. K. Schneiderman, M. E. Vanderlaan, A. M. Mannion, T. R. Panthani, D. C. Batiste, J. Z. Wang, F. S. Bates, C. W. Macosko, M. A. Hillmyer, *ACS Macro Lett.* 2016, 515-518).

Figure 5:
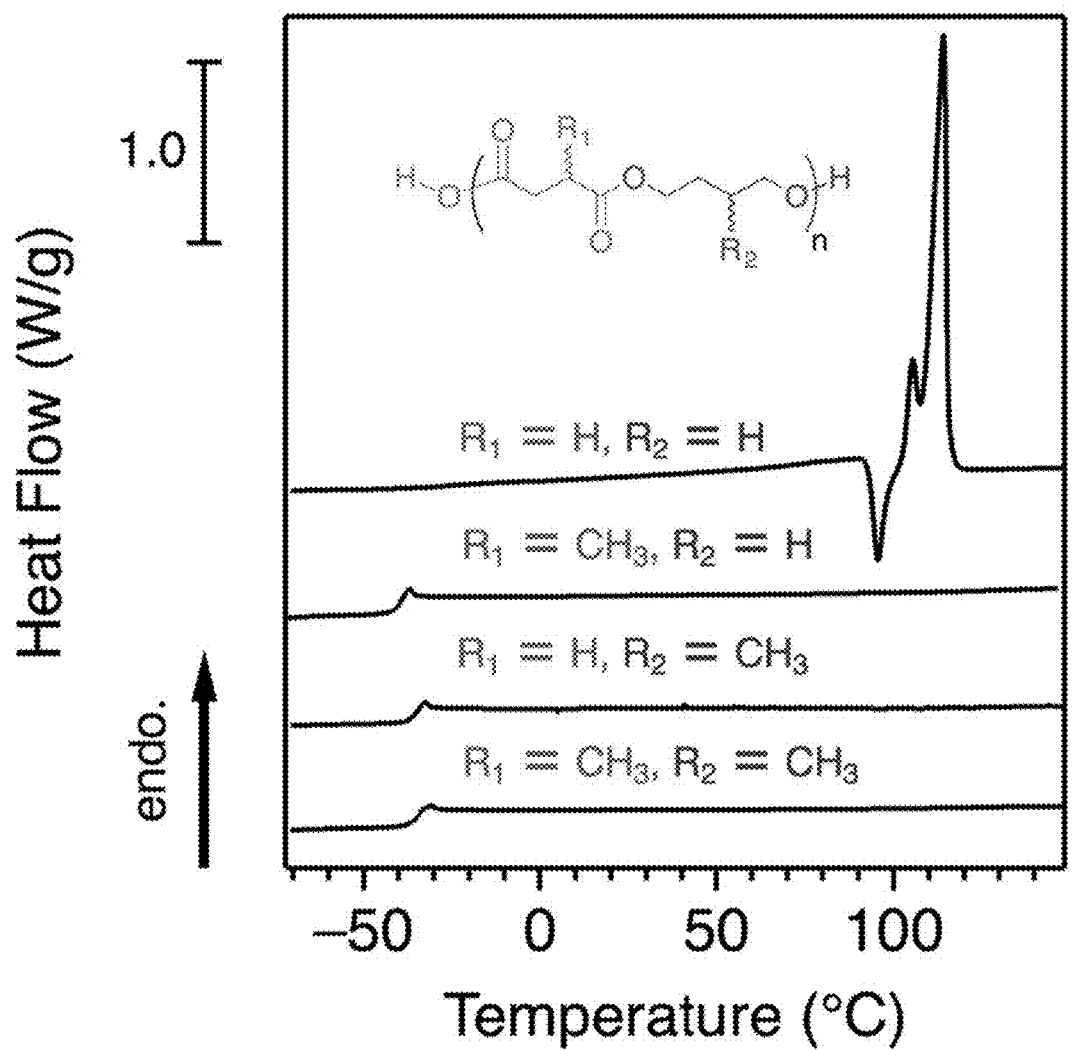
FIG. 5 shows DSC traces comparing the effect of methyl-substitution on glass transition temperature of methyl-substituted poly(butylene succinate) with non-methyl-substituted poly(butylene succinate); the molar masses of these four samples are similar (each is about 10 to 15 kg $mol^{-1}$).
Figure 6:
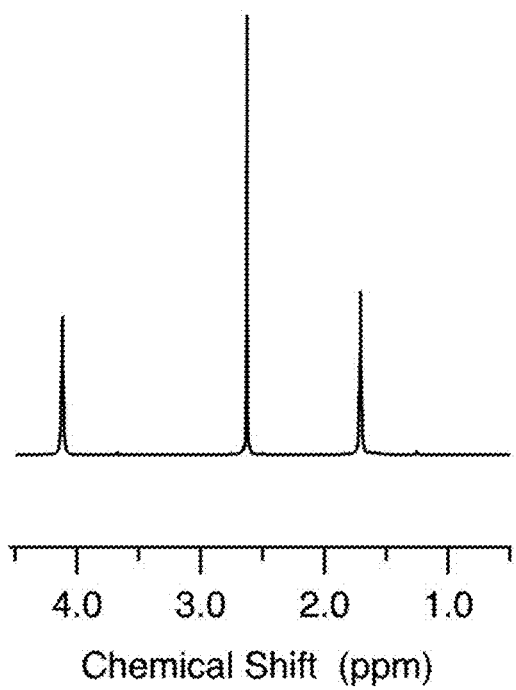
FIG. 6 shows a $^1H$ NMR ($CDCl_3$) spectrum of PBS1.
Figure 7:
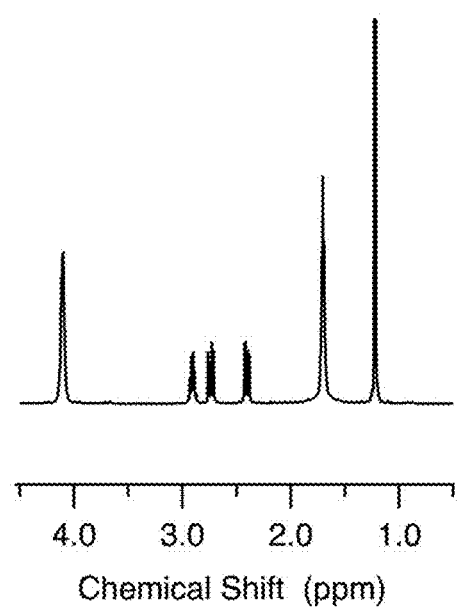
FIG. 7 shows a $^1H$ NMR ($CDCl_3$) spectrum of PBMS-1.
Figure 8:
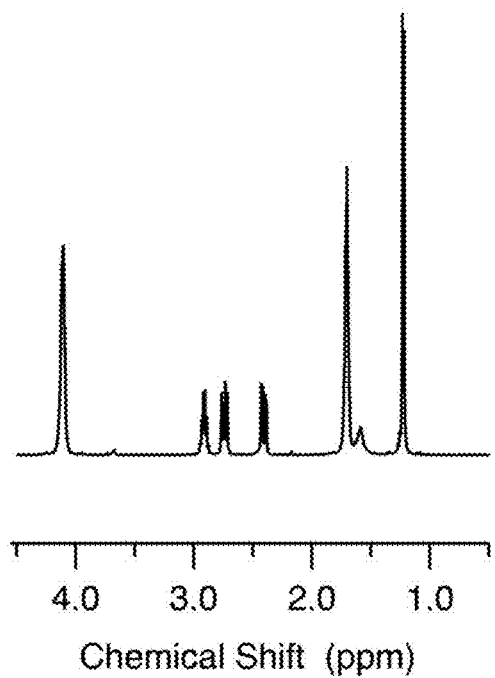
FIG. 8 shows a $^1H$ NMR ($CDCl_3$) spectrum of PBMS-2.
Figure 9:
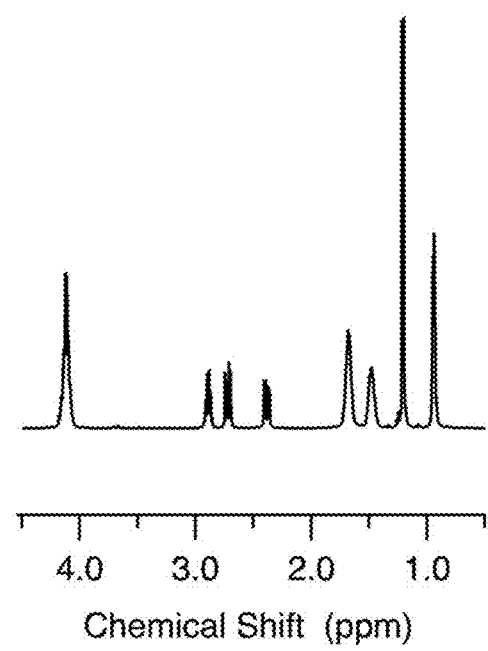
FIG. 9 shows a $^1H$ NMR ($CDCl_3$) spectrum of PMPMS.
Figure 10:
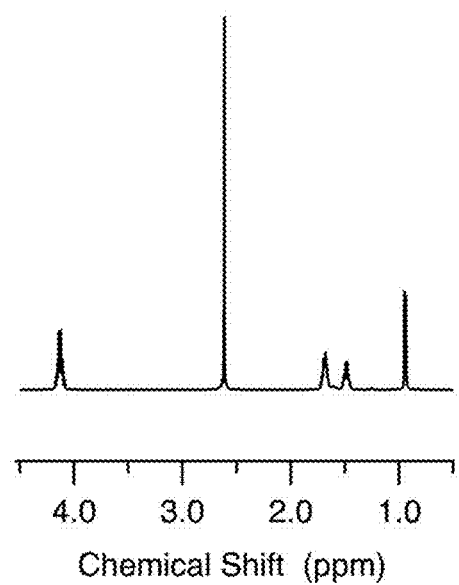
FIG. 10 shows a $^1H$ NMR ($CDCl_3$) spectrum of PMPS.
Figure 11:
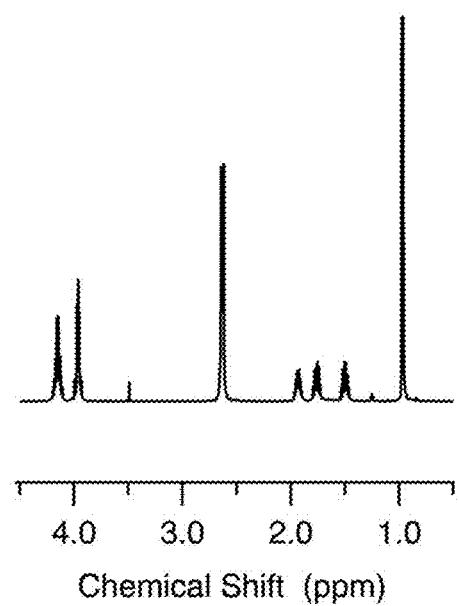
FIG. 11 shows a $^1H$ NMR ($CDCl_3$) spectrum of PMBS.
Figure 12:
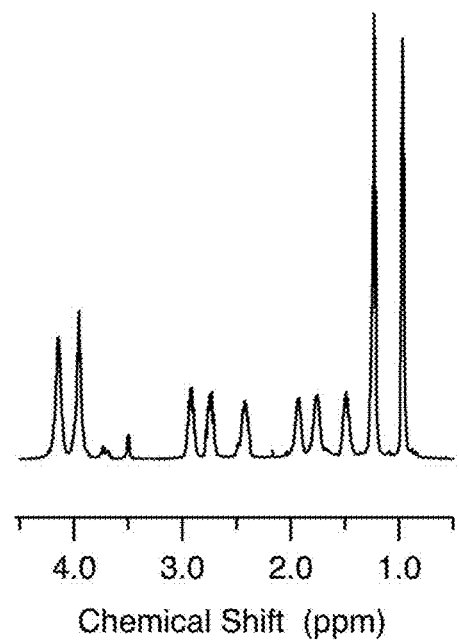
FIG. 12 shows a $^1H$ NMR ($CDCl_3$) spectrum of PMBMS-1.
Figure 13:
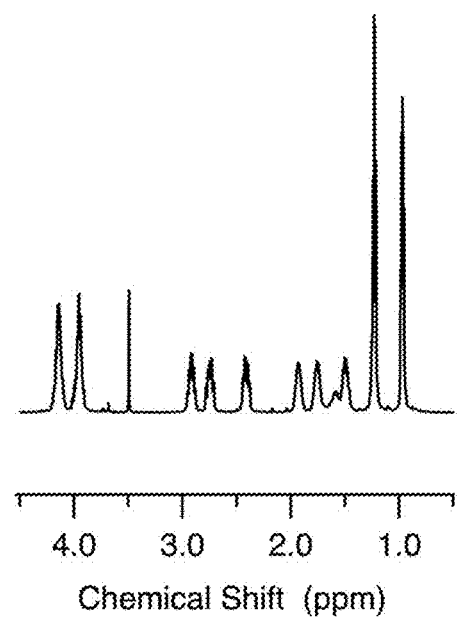
FIG. 13 shows a $^1H$ NMR ($CDCl_3$) spectrum of PMBMS-2.
Figure 14:
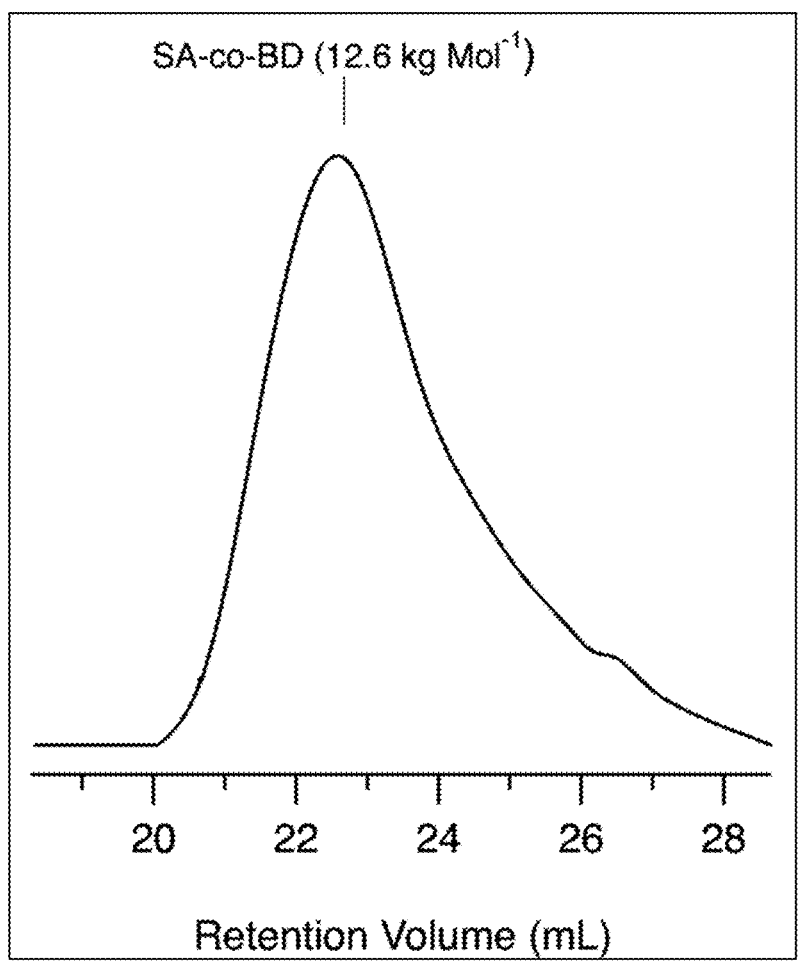
FIG. 14 shows a SEC Chromatograph ($CHCl_3$ mobile phase) of PBS-1.
Figure 15A:
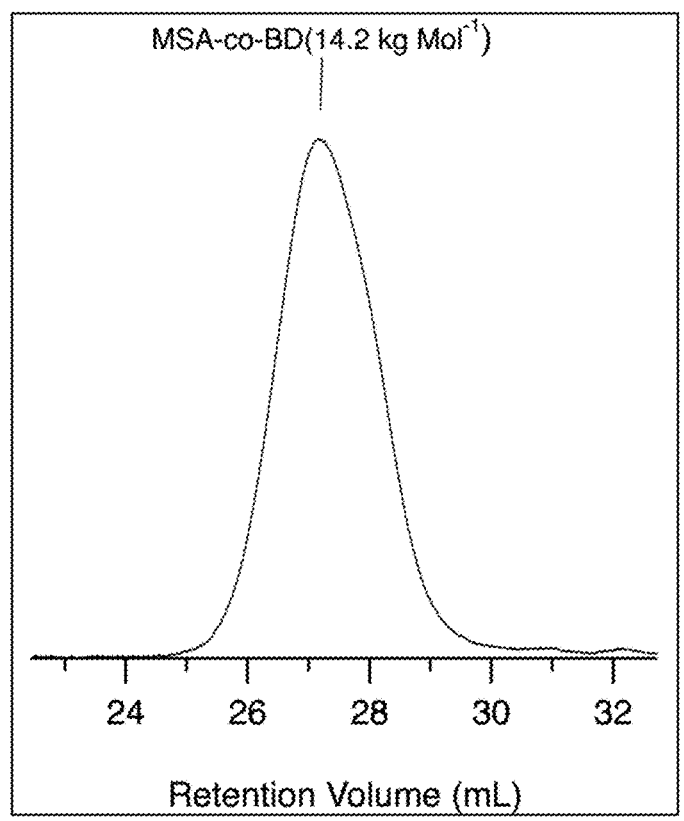
FIGS. 15A and 15B show SEC Chromatograph (THF mobile phase) of PBMS-1 (FIG. 15A) and PBMS-2 (FIG. 15B).
Figure 15B:
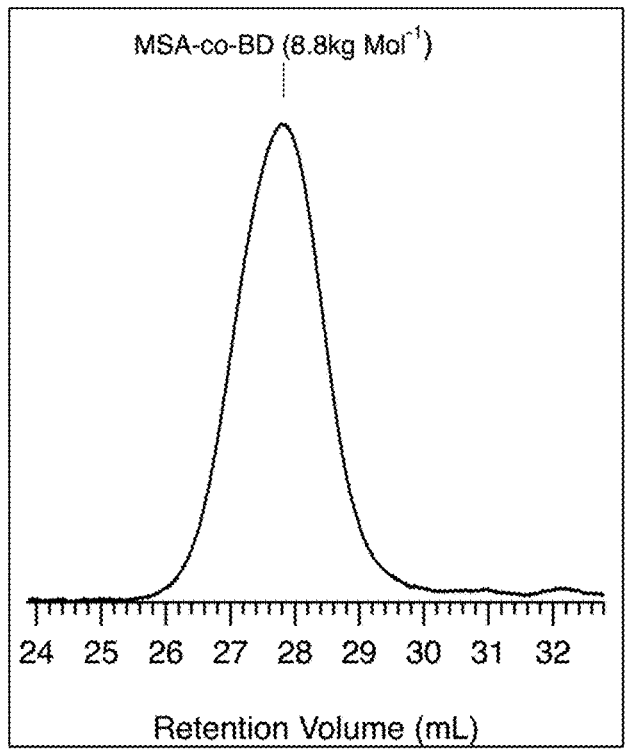
Figure 16:
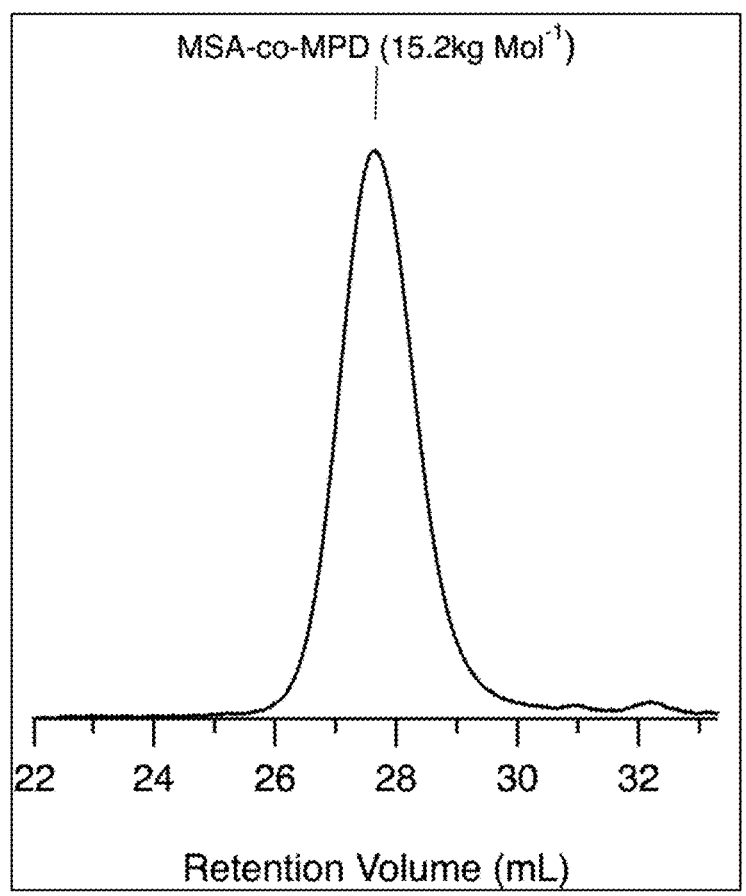
FIG. 16 shows a SEC Chromatograph (THF mobile phase) of PMPMS.

Specifically, FIG. 5 shows DSC traces comparing the effect of methyl-substitution on glass transition temperature of methyl-substituted poly(butylene succinate) with non-methyl-substituted poly(butylene succinate); the molar masses of these four samples are similar (each is about 10 to 15 kg mol$^{-1}$). The synthesis and characterization of these samples is described in further detail below. The polymer structure shown is in some cases over simplified. Because neither 2-methyl-succinic acid nor 2-methyl-1,4-butanediol is symmetric, poly(methylbutylene methylsuccinate), for example, is considerably more complex as the two monomers may be oriented head-to-tail, head-to-head, tail-to-tail, or tail-to-head within the polymer backbone.

Table 4 shows measured characteristics of the prepared polymers.

The specific reagents and conditions utilized to form the polymers can be seen below.

Synthesis of Poly(2-methyl-succinic acid-co-1,4-butanediol) Using Ti(OiPr)$_4$ [Sample Name PBMS-1]

Methyl succinic acid (3.55 g, 0.0269 mol), 1,4-butanediol (2.42 g, 0.0269 mol), and titanium isopropoxide (2.05 µmol, added as a 6 wt. % solution in toluene) were added to a 100 mL round bottom flask along with a magnetic stir bar. Then the round bottom flask was put under vacuum (~10 torr) and heated at 120° C. for 20 h. The reaction flask was then heated to 150° C. and placed under high vacuum (~100 mTorr) for an additional 20 h. After heating at 150° C., the reaction mixture was cooled to room temperature and then dissolved in a minimal amount of chloroform (~30 mL). The dissolved polymer was then precipitated in ~300 mL of methanol and stored overnight at ~20° C. Then the methanol was decanted off and the polymer was dried over air. Then the polymer was put in a vacuum oven overnight at room temperature to dry. The dried sample was obtained in 67% yield.

Synthesis of Poly(2-methyl-succinic acid-co-1,4-butanediol) Using Sn(Oct)$_2$ [Sample Name PBMS-2]

Methyl succinic acid (3.55 g, 0.0269 mol), 1,4-butanediol (2.43 g, 0.0270 mol), and Sn(Oct)$_2$ (2.05 µmol, added as a

TABLE 4

Polymer Characteristics

| Sample | $^a$T$_d$ (° C.) | $^b$T$_g$ (° C.) | $^b$T$_m$ (° C.) | $^c$M$_w$ (kg mol$^{-1}$) | $^e$Đ | $^d$M$_w$ (kg mol$^{-1}$) | $^d$Đ | Yield (%) |
|---|---|---|---|---|---|---|---|---|
| Poly(SA-co-BD) PBS-1 | 266 (326) | −26 | $^e$114 | $^e$12.6 | $^e$3.4 | — | — | 95 |
| Poly(MSA-co-BD) PBMS-1 | 281 (308) | −40 | — | 19.4 | 1.55 | 14.2 | 1.16 | 67 |
| Poly(MSA-co-BD) PBMS-2 | 261 (326) | −39 | — | 12.8 | 1.55 | 8.8 | 1.11 | 78 |
| Poly(MSA-co-MPD) PMPMS | 268 (326) | −42 | — | 14.7 | 2.65 | 15.2 | 1.44 | 71 |
| Poly(SA-co-MPD) PMPS | 277 (334) | −44 | — | 28.1 | 1.87 | 21.7 | 1.37 | 81 |
| Poly(SA-co-MBD) PMBS | 280 (309) | −35 | — | 10.9 | 1.70 | 11.8 | 1.43 | 70 |
| Poly(MSA-co-MBD) PMBMS-1 | 232 | −36 | — | 7.54 | 2.95 | 12.9 | 1.20 | 28 |
| Poly(MSA-co-MBD) PMBMS-2 | 277 (311) | −35 | — | 9.81 | 1.41 | 11.2 | 1.23 | 83 |

$^a$Defined as temperature at which 5% mass loss is observed on TGA heating ramp under air atmosphere with a heating rate of 10° C. min$^{-1}$ the degradation temperature under nitrogen is noted in parentheses. $^b$The T$_g$ and T$_m$ were taken as the inflection point of the transition on the second heating ramp (rate 10° C. min$^{-1}$). $^c$ΔH=83.5 J/g using a reference enthalpy of fusion of PBS (110.3 J/g) (Phua, Y. J.; Chow, W. S.; Mohd Ishak, Z. A. *eXPRESS Polymer Letters* 2011, 5, 93-103), X=76%. $^c$Relative molar mass determined using GPC with a THF mobile phase and RI detector. Values are reported relative to PS standards. $^d$The dn/dc used for MALLS analysis (THF mobile phase) was estimated from the RI signal using the known concentration of the sample with the assumption that 100% of the mass is recovered from the column. $^e$Sample is not soluble in THF, the relative molar mass was determined using GPC with a chloroform mobile phase.

6 wt. % solution in toluene) were added to a 100 mL round bottom flask along with a magnetic stir bar. Then the round bottom flask was put under vacuum (~10 torr) and heated at 120° C. for 20 h. The reaction flask was then heated to 150° C. and placed under high vacuum (~100 mTorr) for an additional 20 h. After heating at 150° C., the reaction mixture was cooled to room temperature and then dissolved in a minimal amount of chloroform (~30 mL). The dissolved polymer was then precipitated in ~300 mL of methanol and stored overnight at −20° C. Then the methanol was decanted off and the polymer was dried over air. Then the polymer was put in a vacuum oven overnight at room temperature to dry. The dried sample was obtained in 78% yield.

Synthesis of Poly(2-methyl-succinic acid-co-3-Methyl-1,5-propanediol) Using Sn(Oct)$_2$ [Sample Name PMPMS]

Methyl succinic acid (2.81 g, 0.0213 mol), 3-methyl-1,5-pentanediol (2.51 g, 0.0212 mol), and Sn(Oct)$_2$ (2.05 µmol, added as a 6 wt. % solution in toluene) were added to a 100 mL round bottom flask along with a magnetic stir bar. Then the round bottom flask was put under vacuum (~10 torr) and heated at 120° C. for 20 h. The reaction flask was then heated to 150° C. and placed under high vacuum (~100 mTorr) for an additional 20 h. After heating at 150° C., the reaction mixture was cooled to room temperature and then dissolved in a minimal amount of chloroform (~30 mL). The dissolved polymer was then precipitated in ~300 mL of methanol and stored overnight at −20° C. Then the methanol was decanted off and the polymer was dried over air. Then the polymer was put in a vacuum oven overnight at room temperature to dry. The dried sample was obtained in 71% yield.

Synthesis of Poly(succinic acid-co-3-Methyl-1,5-propanediol) Using Sn(Oct)$_2$ [Sample Name PMPS]

Succinic acid (2.50 g, 0.0211 mol), 3-methyl-1,5-pentanediol (2.50 g, 0.0212 mol), and Sn(Oct)$_2$ (2.05 µmol, added as a 6 wt. % solution in toluene) were added to a 100 mL round bottom flask along with a magnetic stir bar. Then the round bottom flask was put under vacuum (~10 torr) and heated at 120° C. for 20 h. The reaction flask was then heated to 150° C. and placed under high vacuum (~100 mTorr) for an additional 20 h. After heating at 150° C., the reaction mixture was cooled to room temperature and then dissolved in a minimal amount of chloroform (~30 mL). The dissolved polymer was then precipitated in ~300 mL of methanol and stored overnight at −20° C. Then the methanol was decanted off and the polymer was dried over air. Then the polymer was put in a vacuum oven overnight at room temperature to dry. The dried sample was obtained in 81% yield.

Synthesis of Poly(succinic acid-co-1,4-butanediol) Using Sn(Oct)$_2$ [Sample Name PBS]

Succinic acid (4.084 g, 0.0346 mol, 1,4-butane diol (3.11 g, 0.0345 mol), and Sn(Oct)$_2$ (2.05 µmol, added as a 6 wt. % solution in toluene) were added to a 100 mL round bottom flask along with a magnetic stir bar. Then the round bottom flask was put under nitrogen by means of a bubbler and heated at 185° C. for 20 h. The reaction flask was then cooled to 150° C. and placed under high vacuum (~100 mTorr) for an additional 40 h. After this time the reaction mixture was cooled to room temperature and then dissolved in a minimal amount of chloroform (~100 mL). The dissolved polymer was then precipitated in ~500 mL of methanol and stored overnight at −20° C. Then the methanol was filtered off and the polymer was dried over air. Then the polymer was put in a vacuum oven overnight at room temperature to dry. The dried sample was obtained in 95% yield. Note, unlike the other polymer samples, this sample was analyzed by SEC with a chloroform mobile phase as poly(butylene succinate) is not soluble in THF.

Synthesis of Poly(2-methyl-succinic acid-co-2-methyl-1,4-butanediol) Using Sn(Oct)$_2$ [Sample Name PMBMS-1]

Methyl succinic acid (2.53 g, 0.0191 mol), 2-methyl-1,4-butanediol (2.03 g, 0.0195 mol), and Sn(Oct)$_2$ (2.10 µmol, added as a 6 wt. % solution in toluene) were added to a 100 mL round bottom flask along with a magnetic stir bar. Then the round bottom flask was put under vacuum (~10 torr) and heated at 120° C. for 12 h. The reaction flask was then heated to 150° C. and placed under high vacuum (~100 mTorr) for an additional 12 h. After heating at 150° C., the reaction mixture was cooled to room temperature and then dissolved in a minimal amount of chloroform (~30 mL). The dissolved polymer was then precipitated in ~300 mL of methanol and stored overnight at −20° C. Then the methanol was decanted off and the polymer was dried over air. Then the polymer was put in a vacuum oven overnight at room temperature to dry. The dried sample was obtained in 28% yield.

Synthesis of Poly(2-methyl-succinic acid-co-2-methyl-1,4-butanediol) Using Sn(Oct)$_2$, [Sample Name PMBMS-2]

Methyl succinic acid (1.70 g, 0.0129 mol), 2-methyl-1,4-butanediol (1.33 g, 0.0128 mol), and Sn(Oct)$_2$ (1.00 µmol, added as a 6 wt. % solution in toluene) were added to a 100 mL round bottom flask along with a magnetic stir bar. Then the round bottom flask was put under vacuum (−10 torr) and heated at 120° C. for 24 h. The reaction flask was then heated to 150° C. and placed under high vacuum (~100 mTorr) for an additional 40 h. After heating at 150° C., the reaction mixture was cooled to room temperature and then dissolved in a minimal amount of chloroform (~30 mL). The dissolved polymer was then precipitated in ~300 mL of methanol and stored overnight at −20° C. Then the methanol was decanted off and the polymer was dried over air. Then the polymer was put in a vacuum oven overnight at room temperature to dry. The dried sample was obtained in 83% yield.

Synthesis of Poly(succinic acid-co-2-methyl-1,4-butanediol) Using Sn(Oct)$_2$, [Sample Name PMBS]

Succinic acid (2.27 g, 0.0192 mol), 2-methyl-1,4-butanediol (1.98 g, 0.0190 mol), and Sn(Oct)$_2$ (2.20 µmol, added as a 6 wt. % solution in toluene) were added to a 100 mL round bottom flask along with a magnetic stir bar. Then the round bottom flask was put under vacuum (~10 torr) and heated at 120° C. for 24 h. The reaction flask was then heated to 150° C. and placed under high vacuum (~100 mTorr) for an additional 24 h. After heating at 150° C., the reaction mixture was cooled to room temperature and then dissolved in a minimal amount of chloroform (~30 mL). The dissolved polymer was then precipitated in ~300 mL of methanol and stored overnight at ~20° C. Then the methanol was decanted off and the polymer was dried over air. Then the polymer was put in a vacuum oven overnight at room temperature to dry. The dried sample was obtained in 70% yield.

$^1$H NMR spectra of polymer samples are reported as the average of at least 16 scans and were acquired using a 5 second acquisition time and a 10 second delay. The spectra are shown in FIGS. 6 to 13.

The polymer samples were also analyzed by SEC with a chloroform mobile phase as poly(butylene succinate) is not soluble in THF. The chromatograms are shown below in FIGS. 14 to 19.

Figure 20:
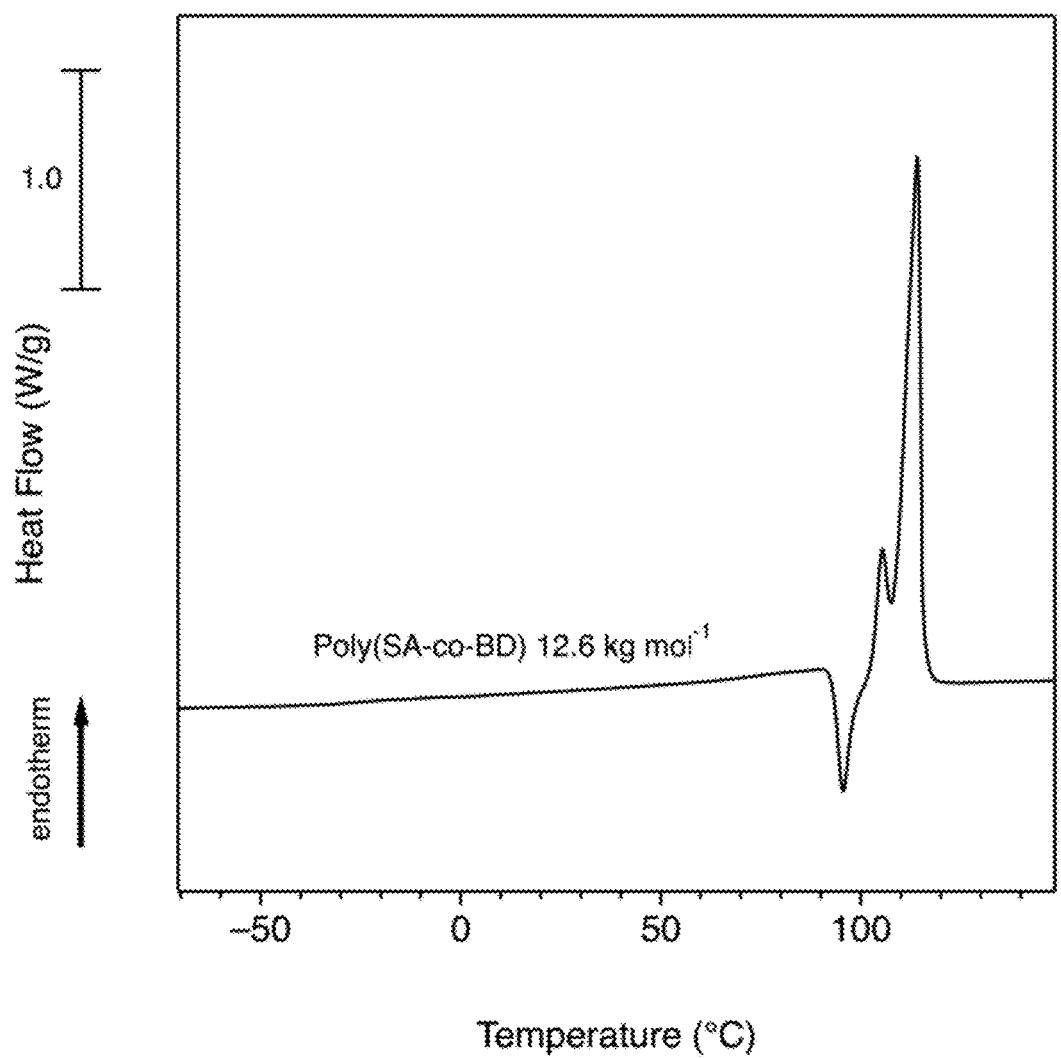
FIG. 20 shows a DSC of poly(2-succinic acid-co-1,4-butanediol). Data shown are second heating ramp (10° C. $min^{-1}$).
Figure 21:
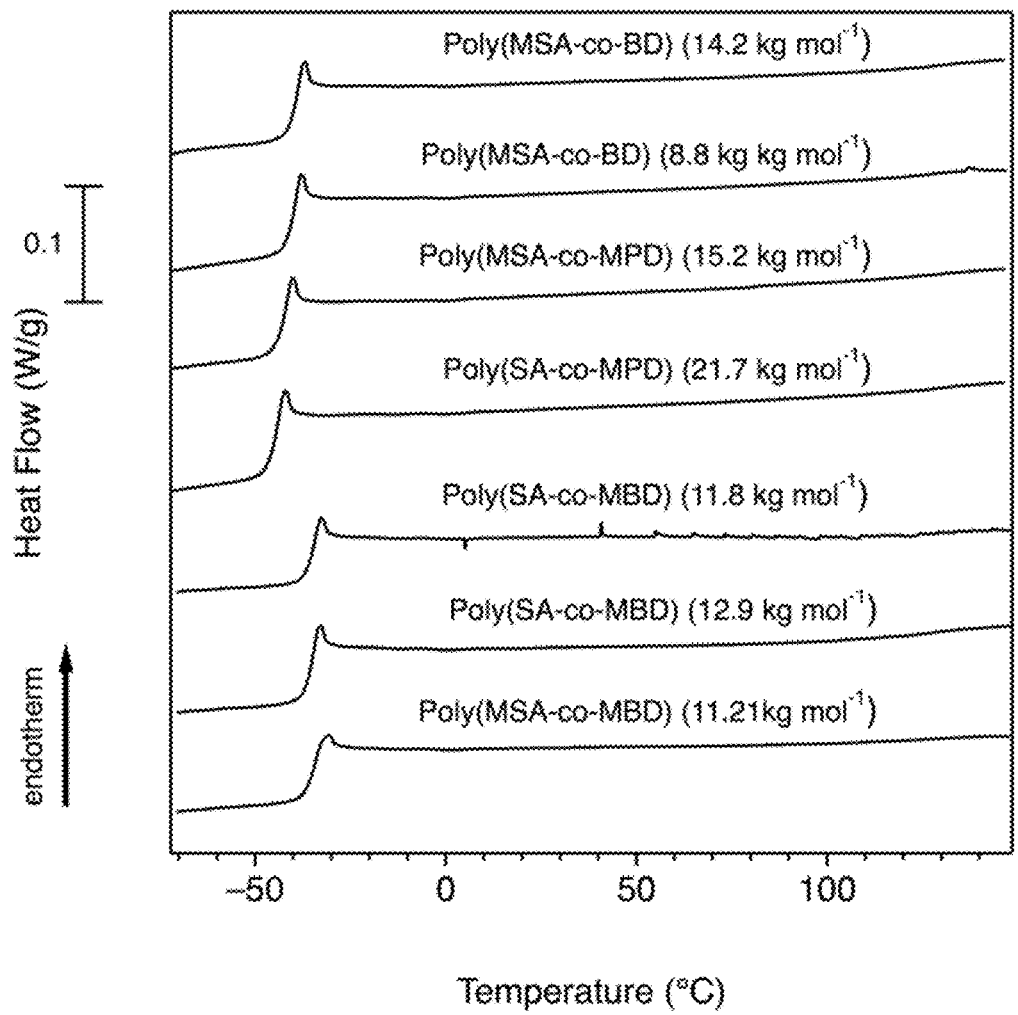
FIG. 21 shows a DSC overlay of amorphous polymer samples shown in Table 4. Data shown are second heating ramp (10° C. $min^{-1}$).

DSC traces of the polymers were also gathered. FIGS. 20 and 21 show some of these traces.

Figure 22:
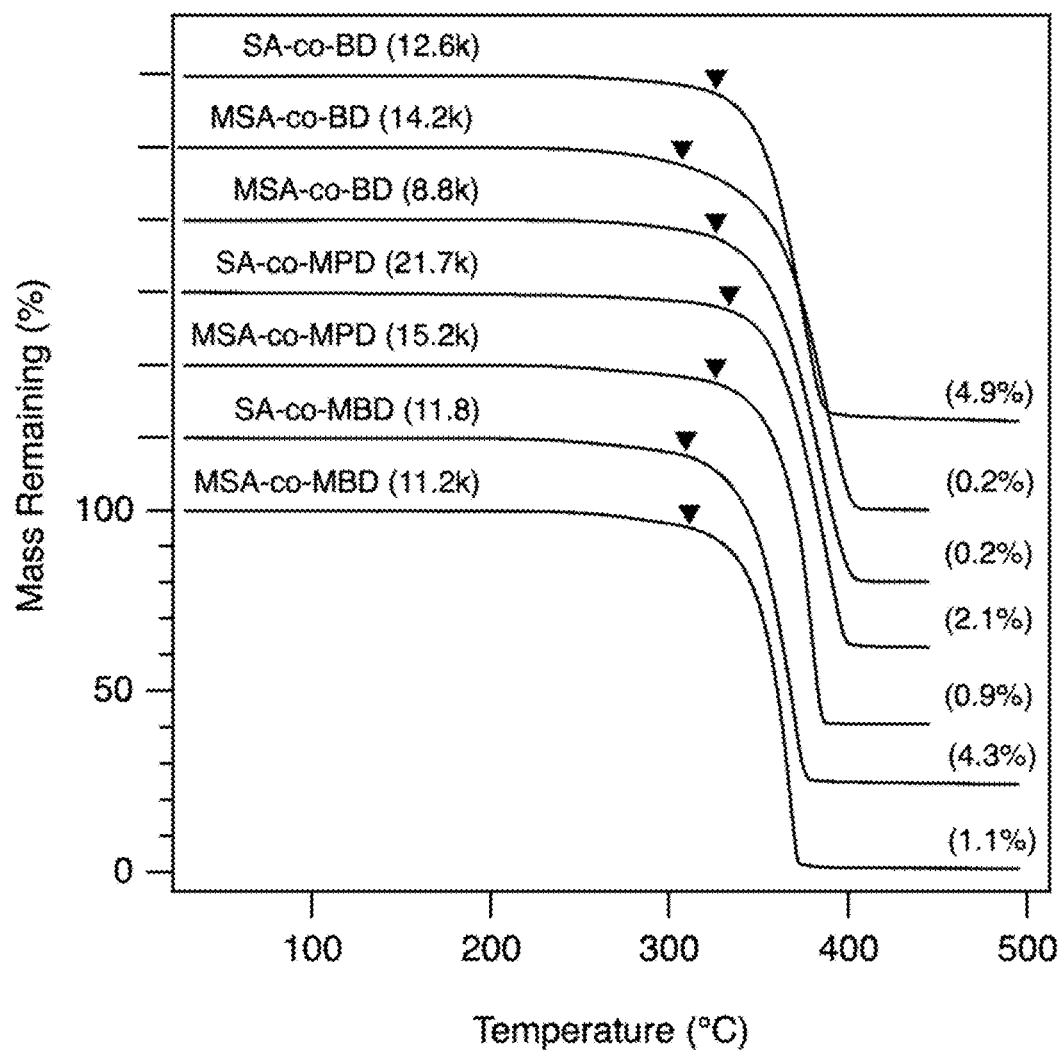
FIG. 22 shows a TGA overlay (nitrogen atmosphere, ramp rate 10° C. $min^{-1}$) of polymer samples detailed in Table 4.
Figure 23:
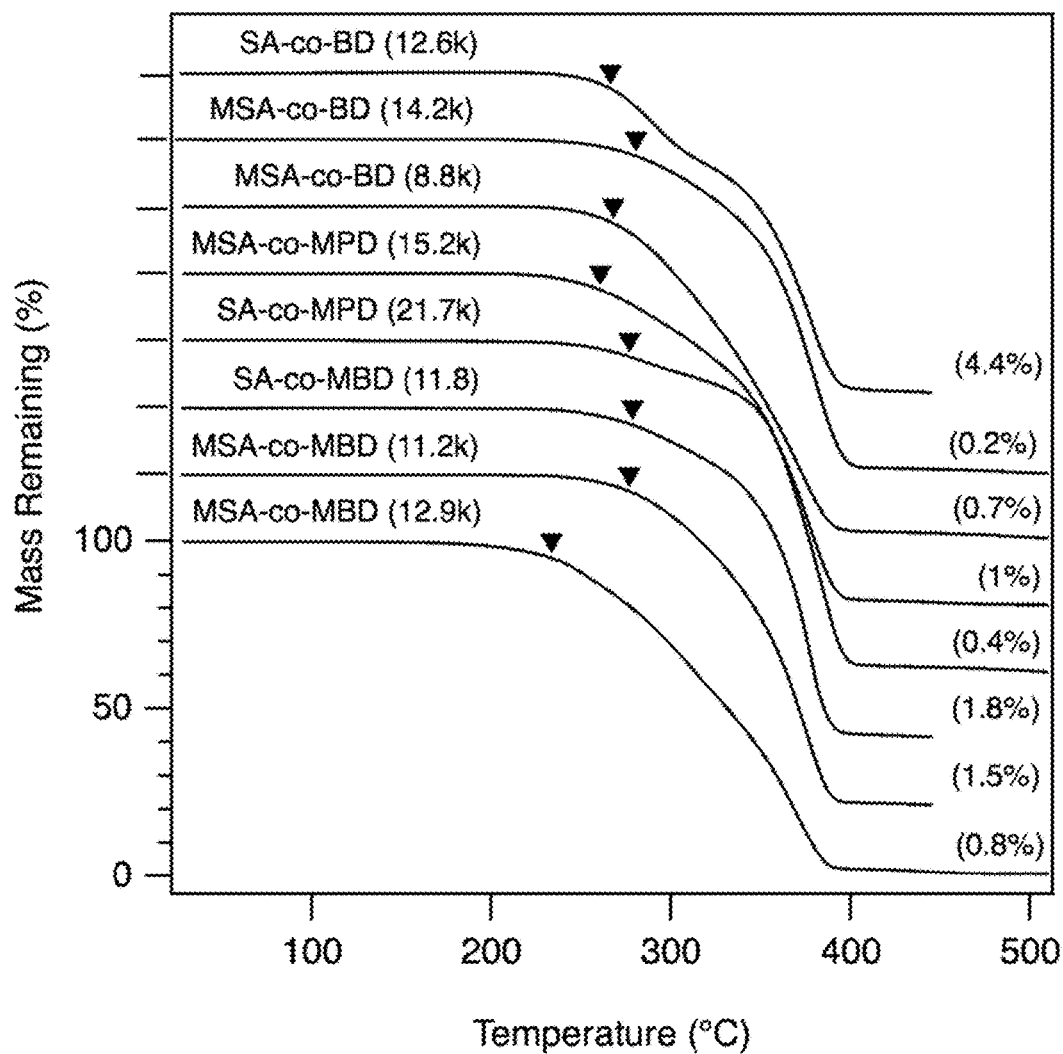
FIG. 23 shows a TGA overlay (air atmosphere, ramp rate 10° C. $min^{-1}$) of polymer samples detailed in Table 4.

TGA was also carried out on the polymers. FIGS. 22 and 23 show the results thereof

The invention claimed is:

1. A method of forming a $C_4$ to $C_7$ diol compound, the method comprising:

a first step of reacting a $C_4$ to $C_7$ dicarboxylic acid with hydrogen ($H_2$) gas on a first heterogeneous catalyst at a first temperature and a first pressure to form a $C_4$ to $C_7$ lactone; and a subsequent step of reacting the lactone with hydrogen ($H_2$) gas on a second heterogeneous catalyst at a second temperature and a second pressure, wherein the second temperature is lower than the first temperature.

2. The method according to claim 1, wherein the $C_4$ to $C_7$ diol compound to be formed is a compound of formula I

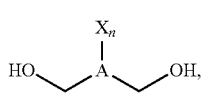

(I)

where X is independently selected from H, —OH, alkyl, alkenyl; n is 1 or 2; and A is a $C_2$ to $C_4$ substituted or unsubstituted alkyl radical or a $C_2$ to $C_4$ substituted or unsubstituted alkenyl radical.

3. The method according to claim 2, wherein the $C_4$ to $C_7$ dicarboxylic acid is a dicarboxylic acid of formula II

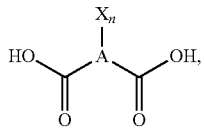

(II)

and the $C_4$ to $C_7$ dicarboxylic acid is converted to a lactone of formula III

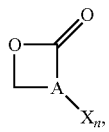

(III)

wherein X, A, and n are as defined in claim 2.

4. The method of claim 1, wherein the first heterogeneous catalyst comprises palladium (Pd), platinum (Pt), rhodium (Rh), ruthenium (Ru), nickel (Ni), copper chromite ($Cu_2Cr_2O_5$), or combinations thereof.

5. The method of claim 1, wherein the first temperature is at least 160° C.

6. The method of claim 1, wherein the first pressure is at least about 35 bar.

7. The method of claim 1, wherein the second heterogeneous catalyst comprises ruthenium (Ru), palladium (Pd), platinum (Pt), rhenium (Re), or combinations thereof.

8. The methods of claim 1, wherein the second temperature is less than about 150° C.

9. The method of claim 1, wherein the second pressure is at least about 100 bar.

10. The method of claim 1, wherein both the first and the second step are done in an aqueous environment.

11. The method of claim 1, wherein the dicarboxylic acid is selected from itaconic acid (IA), mesaconic acid (MA), glutaric acid, glutaconic acid, adipic acid, muconic acid, succinic acid, fumaric acid, maleic acid, mevalonic acid, citaconic acid, methylsuccinic, and malic acid.

12. The method of claim 1, wherein the dicarboxylic acids are in a composition derived from biomass.

13. The method of claim 1 further comprising converting the diols into branched polymers.

14. A method of forming a polymer, the method comprising:

a first step of reacting a $C_4$ to $C_7$ dicarboxylic acid according to formula II

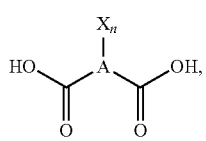

(II)

where X is independently selected from H, —OH, alkyl, alkenyl; n is 1 or 2; and A is a $C_2$ to $C_4$ substituted or unsubstituted alkyl radical or a $C_2$ to $C_4$ substituted or unsubstituted alkenyl radical with hydrogen ($H_2$) gas on a first heterogeneous catalyst at a first temperature and a first pressure to form a $C_4$ to $C_7$ lactone of formula III

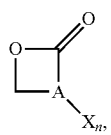

(III)

wherein X, A and n are as defined above;

a subsequent step of reacting the lactone of formula III with hydrogen ($H_2$) gas on a second heterogeneous catalyst at a second temperature and a second pressure to form a diol of formula I

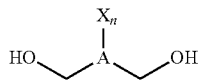

(I)

where X, A and n are as defined above, wherein the second temperature is lower than the first temperature; and a further step of converting the diol of formula I into branched polymers.

15. The method according to claim 14, wherein the first heterogeneous catalyst comprises palladium (Pd), platinum (Pt), rhodium (Rh), ruthenium (Ru), nickel (Ni), copper chromite ($Cu_2Cr_2O_5$), or combinations thereof.

16. The method according to claim 14, wherein the second heterogeneous catalyst comprises ruthenium (Ru), palladium (Pd), platinum (Pt), rhenium (Re), or combinations thereof.

17. The method according to claim 14, wherein the first temperature is at least 160° C.; and the second temperature is less than about 150° C.

* * * * *